United States Patent
Chao

(10) Patent No.: US 10,399,924 B2
(45) Date of Patent: Sep. 3, 2019

(54) DEUTERIUM SUBSTITUTED FUMARATE DERIVATIVES

(71) Applicant: Biogen MA Inc., Cambridge, MA (US)

(72) Inventor: Jianhua Chao, Cambridge, MA (US)

(73) Assignee: Biogen MA Inc., Cambridge, MA (US)

( * ) Notice: Subject to any disclaimer, the term of this patent is extended or adjusted under 35 U.S.C. 154(b) by 189 days.

(21) Appl. No.: 14/201,380

(22) Filed: Mar. 7, 2014

(65) Prior Publication Data
US 2014/0194427 A1    Jul. 10, 2014

Related U.S. Application Data

(63) Continuation of application No. PCT/US2013/077248, filed on Dec. 20, 2013.
(Continued)

(51) Int. Cl.
*A61K 31/22* (2006.01)
*C07C 69/60* (2006.01)
(Continued)

(52) U.S. Cl.
CPC ............ *C07C 69/60* (2013.01); *A61K 31/225* (2013.01); *A61K 31/235* (2013.01); *A61K 31/24* (2013.01); *A61K 31/5375* (2013.01); *A61K 45/06* (2013.01); *C07B 59/001* (2013.01); *C07C 69/533* (2013.01); *C07C 69/76* (2013.01); *C07C 229/36* (2013.01); *C07D 295/145* (2013.01)

(58) Field of Classification Search
CPC .................................................. A61K 31/215
USPC ........................................ 514/549; 560/190
See application file for complete search history.

(56) References Cited

U.S. PATENT DOCUMENTS 6,277,882 B1   8/2001   Joshi et al.
6,355,676 B1   3/2002   Joshi et al.
(Continued)

FOREIGN PATENT DOCUMENTS

WO   WO 2006/037342 A2   4/2006
WO   WO 2006/050730 A1   5/2006
(Continued)

OTHER PUBLICATIONS

Marling and Herman, Deuterium separation with 1400-fold single-step isotopic enrichment and high yield by CO2-laser multiple-photon dissociation of 2,2-dichloro-1,1,1- trifluoroethane, Applied Physics Letters, vol. 34, Issue 7, id. 439 (1979).*
(Continued)

*Primary Examiner* — Shengjun Wang
(74) *Attorney, Agent, or Firm* — Jones Day

(57) ABSTRACT

Provided herein are deuterium substituted fumarate derivatives and pharmaceutical compositions comprising deuterium substituted fumarate derivatives. Also provided is a method of treating, prophylaxis, or amelioration of a disease, comprising administering to a subject in need of treatment for the disease an effective amount of a deuterium substituted fumarate derivative or a pharmaceutical composition comprising a deuterium substituted fumarate derivative. In one embodiment, the method is a neurodegenerative disease, such as multiple sclerosis, amyotrophic lateral sclerosis, Parkinson's disease, Huntington's disease, or Alzheimer's disease.

29 Claims, 6 Drawing Sheets

Specification includes a Sequence Listing.

Related U.S. Application Data

(60) Provisional application No. 61/745,115, filed on Dec. 21, 2012.

(51) Int. Cl.

| | |
|---|---|
| *C07C 69/533* | (2006.01) |
| *A61K 31/225* | (2006.01) |
| *A61K 31/235* | (2006.01) |
| *A61K 31/24* | (2006.01) |
| *A61K 31/5375* | (2006.01) |
| *A61K 45/06* | (2006.01) |
| *C07C 69/76* | (2006.01) |
| *C07C 229/36* | (2006.01) |
| *C07D 295/145* | (2006.01) |
| *C07B 59/00* | (2006.01) |

(56) References Cited

U.S. PATENT DOCUMENTS

| | | | |
|---|---|---|---|
| 6,359,003 | B1 | 3/2002 | Joshi et al. |
| 6,436,992 | B1 | 8/2002 | Joshi et al. |
| 6,509,376 | B1 | 1/2003 | Joshi et al. |
| 6,858,750 | B2 | 2/2005 | Joshi et al. |
| 7,157,423 | B2 | 1/2007 | Joshi et al. |
| 7,320,999 | B2 | 1/2008 | Joshi et al. |
| 7,432,240 | B2 | 10/2008 | Joshi et al. |
| 7,612,110 | B2 | 11/2009 | Joshi et al. |
| 7,619,001 | B2 | 11/2009 | Joshi et al. |
| 7,790,916 | B2 | 9/2010 | Joshi et al. |
| 7,803,840 | B2 | 9/2010 | Joshi et al. |
| 7,906,659 | B2 | 3/2011 | Joshi et al. |
| 7,915,310 | B2 | 3/2011 | Joshi et al. |
| 8,067,467 | B2 | 11/2011 | Joshi et al. |
| 8,399,514 | B2 | 3/2013 | Lukashev et al. |
| 8,524,773 | B2 | 9/2013 | Joshi et al. |
| 2004/0054001 | A1 | 3/2004 | Joshi et al. |
| 2007/0027076 | A1 | 2/2007 | Joshi et al. |
| 2008/0233185 | A1 | 9/2008 | Joshi et al. |
| 2009/0304790 | A1 | 12/2009 | Nilsson et al. |
| 2010/0130607 | A1 | 5/2010 | Gold |
| 2011/0112196 | A1 | 5/2011 | Lukashev |
| 2011/0124615 | A1 | 5/2011 | Joshi et al. |
| 2011/0160253 | A1 | 6/2011 | Harbeson |
| 2011/0293711 | A1 | 12/2011 | Joshi et al. |
| 2012/0165404 | A1 | 6/2012 | Lukashev |
| 2012/0259012 | A1 | 10/2012 | Lukashev |
| 2013/0065909 | A1* | 3/2013 | Milne ............... A61K 47/481 514/255.01 |
| 2013/0216615 | A1 | 8/2013 | Goldman |
| 2013/0287732 | A1 | 10/2013 | Goelz et al. |
| 2013/0295169 | A1 | 11/2013 | Goldman et al. |
| 2013/0302410 | A1 | 11/2013 | Gold |
| 2013/0303613 | A1 | 11/2013 | Lukashev |
| 2013/0315993 | A1 | 11/2013 | Nilsson et al. |
| 2013/0316003 | A1 | 11/2013 | Nilsson et al. |
| 2013/0317103 | A1 | 11/2013 | Lukashev |
| 2014/0037740 | A1 | 2/2014 | Nilsson et al. |
| 2014/0066505 | A1 | 3/2014 | Joshi et al. |
| 2014/0099364 | A2 | 4/2014 | Nilsson et al. |

FOREIGN PATENT DOCUMENTS

| | | |
|---|---|---|
| WO | WO 2007/006307 A2 | 1/2007 |
| WO | WO 2007/006308 A1 | 1/2007 |
| WO | WO 2007/042034 A1 | 4/2007 |
| WO | WO 2007/042035 A2 | 4/2007 |
| WO | WO 2010/126605 A1 | 11/2010 |
| WO | WO 2012/162669 A1 | 11/2012 |
| WO | WO 2012/170923 A1 | 12/2012 |
| WO | WO 2013/090799 A1 | 6/2013 |
| WO | WO 2013/119677 A1 | 8/2013 |
| WO | WO 2015/027949 | 3/2015 |

OTHER PUBLICATIONS

Gold, R. et al., N Engl J Med 2012; 367:1098-1107 Sep. 20, 2012 DOI: 10.1056/NEJMoa1114287.*
Kushner, DJ et al., Can J Physiol Pharmacol. Feb. 1999;77(2):79-88.*
Kenda et al. "Fundamental of isotope Geochemistry," Chapter 2, Isotope Tracers in Catchment Hydrology, 1998, C. Kendall and J.J.McDonnell (Eds.) Elsevier Science B. V. Amsterdam. (Year: 1998).*
Harbeson et al. "Deuterium in Drug Discovery and developments," Annual Report in Medicinal Chemistry, vol. 46, 2011, pp. 403-417. (Year: 2011).*
Barclay et al., 1996, "Synthesis of (2S)-O-phosphohomoserine and its C-2 deuteriated and C-3 chirally deuteriated isotopomers: probes for the pyridoxal phosphate-dependent threonine synthase reaction" Journal of the Chemical Society, 1:683-689.
Cochran et al., 1989, "Protodestannylation of carbomethoxy-substituted vinylstannanes: kinetics, stereochemistry, and mechanisms", Organometallics, 8(3):804-812.
Cochran et al., 1989, "Protodestannylation of carbomethoxy-substituted vinylstannanes: kinetics, stereochemistry, and mechanisms", Organometallics, 8(3):804-812 (erratum to NPL88).
Hung-Low et al., 2012, "sp$^2$C—H activation of dimethyl fumarate by a [(Cp * Co)$_2$-μ-($\eta^4$:$\eta^4$toluene)] complex", Dalton Transactions, 41(26):8190-8197.
Lee and Spitzer, 1976, "The oxidation of methyl cinnamate by ruthenium tetroxide" The Journal of Organic Chemistry, 41(22):3644.
Lee et al., 1989, "A highly effective and large-scale synthesis of (2S, 3S)-[2,3-$^2$H$_2$]-and (2S, 3R)-[3-$^2$H] aspartic acids via an immobilized aspartase-containing microbial cell system", The Journal of Organic Chemistry, 54(13):3195-3198.
Lobell and Crout, 1996, "New insight into the pyruvate decarboxylase-catalysed formation of lactaldehyde from H-D exchange experiments: a 'water proof' active site", Journal of the Chemical Society, 1:1577-1581.
Marling and Herman, 1984, "Deuterium separation with 1400-fold single-step isotopic enrichment and high yield by CO2-laser multiple-photon dissociation of 2,2,-dichloro-1,1,1-trifluoroethane", Appl. Physics Lett. 34(7):439-442.
Pereyre et al., 1971, "Synthèse de composés organiques deutériés par l'intermédiaire de deutériures et d'hydrures organostanniques", Organometallics in Chemical Synthesis, 1(3):269-288.
Richards et al., 1969, "Reactions of phosphines with acetylenes. Part VIII. Synthesis of 1,2-dideuteriated olefins", Journal of the Chemical Society (C):1542-1544.
Shiotsuki et al., 2000,"Reaction of Ru(1-6-η-cyclooctotriene) ($\eta^2$-dimethyl fumarate)$_2$ with monodentate and bidentate phosphines:a model reaction of catalytic dimerization of alkenes", Organometallics, 19(26):5733-5743.
Tsujita et al., 2005, "Synthesis of 2-alkylidenetetrahydrofurans by Ru-catalyzed regio- and stereoselective codimerization of dihydrofurans with α,β-unsaturated esters", Chemical Communications, 40:5100-5102.
Werner et al., 1972, "Darstellung selektiv deuterierter cyclohexen- and cyclohexanderivate für NMR-Untersuchungen", Zeitschrift fuer Chemie, 12(7):262-263.
Xia et al., 2007, "An unexpected role of a trace amount of water in catalyzing proton transfer in phosphine-catalyzed (3+2) cycloaddition of allenoates and alkenes", Journal of the American Chemical Society.
Yan et al., 1984, "Stereochemistry of the ethanolamine ammonia lyase reaction with stereospecifically labeled [1 -$^2$H$_1$]-2-aminoethanol", Journal of the American Chemical Society, 106(10):2961-2964.
Zhu and Falck, 2012, "Rhodium catalyzed C—H olefination of N-benzoylsulfonamides with internal alkenes", Chemical Communications, 48(11):1674-1676.
Document entitled "Evaluation of the pharmacokinetic properties of Example 4 against DMF in 0.5% HPMC".
Aminzadeh, M.A., et al. "The synthetic triterpenoid RTA dh404 (CDDO-dhTFEA) restores Nrf2 activity and attenuates oxidative stress, inflammation, and fibrosis in rats with chronic kidney disease," *Xenobiotica, Early Online:* 1-9, Informa UK Ltd., England (2013).

(56) References Cited

OTHER PUBLICATIONS

Baxter, A.G., et al., "High and Low Diabetes Incidence Nonobese Diabetic (NOD) Mice: Origins and Characterization," *Autoimmunity* 9:61-67, Harwood Academic Publishers GmbH, United Kingdom (1991).

Berge, S.M., et al., "Pharmaceutical Salts," *Journal of Pharmaceutical Sciences* 66(1):1-19, American Pharmaceutical Assn., United States (1977).

Beyer, C., et al., "Animal Models of Systemic Sclerosis," *Arthritis & Rheumatism* 62(10):2831-44, American College of Rheumatology, United States (2010).

Bhattacharyya, S., et al., "Understanding fibrosis in systemic sclerosis: shifting paradigms, emerging opportunities," *Nature Reviews Rheumatology* 8:42-54, Macmillan Publishers Limited, United States (2012).

Blesa, J., et al., "Classic and New Animal Models of Parkinson's Disease," *Journal of Biomedicine and Biotechnology* 2012:845618, Hindawi Publishing Corporation, United States (2012).

Calkins, M.J., et al., "Astrocyte-Specific Overexpression of Nrf2 Protects Striatal Neurons from Mitochondrial Complex II Inhibition," *Toxicological Sciences* 115(2):557-68, Oxford University Press, United States (2010).

Chen, X-L and Kunsch, C., "Induction of Cytoprotective Genes Through Nfr2/Antioxidant Response Element Pathway: A New Therapeutic Approach for the Treatment of Inflammatory Diseases," *Current Pharmaceutical Design* 10:879-91, Bentham Science Publishers Ltd., Netherlands (2004).

Cho, H-Y, et al., "Nrf2-regulated PPARγ Expression is Critical to Protection against Acute Lung Injury in Mice," *Am J Respir Crit Care Med* 182:170-82, American Thoracic Society, United States (2010).

Christmann, R.B., et al., "Thymic stromal lymphopoietin is up-regulated in the skin of patients with systemic sclerosis and induces profibrotic genes and intracellular signaling that overlap with those induced by interleukin-13 and transforming growth factor β," *Arthritis & Rheumatism* 65(5):1335-46, American College of Rheumatology, United States (May 2013).

Dadras, F., et al., "NF-E2-related Factor 2 and Its Role in Diabetic Nephropathy," *Iranian Journal of Kidney Diseases* 7(5):346-51, Iranian Society of Nephrology, Iran (2013).

Dinkova-Kostova, A.T., et al., "Extremely potent triterpenoid inducers of the phase 2 response: Correlations of protection against oxidant and inflammatory stress," *Proceedings of the National Academy of Sciences of the United States of America* 102(12):4584-89, National Academy of Sciences, United States (2005).

Ellrichmann, G., et al., "Efficacy of Fumaric Acid Esters in the R6/2 and YAC128 Models of Huntington's Disease," *PLoS One* 6(1):e16172, Public Library of Science, United States (2011).

Ercolini, A.M. and Miller, S.D., "Mechanisms of Immunopathology in Murine Models of Central Nervous System Demyelinating Disease," *The Journal of Immunology* 176:3293-98, The American Association of Immunologists, Inc., United States (2006).

Fox, R.J., et al., "Placebo-Controlled Phase 3 Study of Oral BG-12 or Glatiramer in Multiple Sclerosis," *The New England Journal of Medicine* 367(12):1087-97, Massachusetts Medical Society, United States (2012).

Gold, R., et al., "Placebo-Controlled Phase 3 Study of Oral BG-12 for Relapsing Multiple Sclerosis," *The New England Journal of Medicine* 367(12):1098-1107, Massachusetts Medical Society, United States (2012).

Götz, J. and Ittner, L.M., "Animal models of Alzheimer's disease and frontotemporal dementia," *Nature Reviews Neuroscience* 9:532-544, Macmillan Publishers Limited, United States (2008).

Hanson, J., et al., "Nicotinic acid- and monomethyl fumarate-induced flushing involves GPR109A expressed by keratinocytes and COX-2-dependent prostanoid formation in mice," Journal of Clinical Investigation 120(8):2910-19, American Society for Clinical Investigation, United States (2010).

Hanson, J., et al., "Role of $HCA_2$ (GPR109A) in nicotinic acid and fumaric acid ester-induced effects on the skin," *Pharmacology & Therapeutics* 136:1-7, Pergamon Press, England (Oct. 2012).

Hecker, L., et al., "NADPH Oxidase-4 Mediates Myofibroblast Activation and Fibrogenic Responses to Lung Injury," *Nature Medicine* 15(9):1077-81, Nature Publishing Company, United States (2009).

Hinz, B., et al., "Recent Developments in Myofibroblast Biology: Paradigms for Connective Tissue Remodeling," *The American Journal of Pathology* 180(4):1340-55, Elsevier Inc., United States (2012).

Ishida, W., et al., "Intracellular TGF-β Receptor Blockade Abrogates Smad-Dependent Fibroblast Activation in Vitro and in Vivo," *The Journal of Investigative Dermatology* 126:1733-44, The Society for Investigative Dermatology, United States (2006).

Ji, H., et al., "Different modes of pathogenesis in T-cell-dependent autoimmunity: clues from two TCR transgenic systems," *Immunological Reviews* 169:139-46, Munksgaard, Denmark (1999).

Katsnelson, A., "Heavy drugs draw heavy interest from pharma backers," *Nature Medicine* 19:656, Nature Publishing Company, United States (Jun. 2013).

Kikuchi, N., et al., "Nrf2 protects against pulmonary fibrosis by regulating the lung oxidant level and Th1/Th2 balance," *Respiratory Research* 11:31, BioMed Central Ltd., England (2010).

Kwak, M.-K., et al., "Modulation of Gene Expression by Cancer Chemopreventive Dithiolethiones through the Keap1-Nrf2 Pathway," *The Journal of Biological Chemistry* 278(10):8135-45, The American Society for Biochemistry and Molecular Biology, Inc., United States (2003).

Larpent, C. and Patin, H., "A New Synthesis of Vinylphosphonium Salts. Application for Deuterium Labeling," *Tetrahedron Letters* 29(36):4577-80, Pergamon Press plc, Great Britain (1988).

Lee, J-M, et al., "Identification of the NF-E2-related Factor-2-dependent Genes Conferring Protection against Oxidative Stress in Primary Cortical Astrocytes Using Oligonucleotide Microarray Analysis," *J. Biol. Chem.* 278(14):12029-12038, The American Society for Biochemistry and Molecular Biology, Inc., United States (2003).

Liby, K.T. and Sporn, M.B., "Synthetic Oleanane Triterpenoids: Multifunctional Drugs with a Broad Range of Applications for Prevention and Treatment of Chronic Disease," *Pharmacological Reviews* 64(4):972-1003, The American Society for Pharmacology and Experimental Therapeutics, United States (2012).

Linker, R.A., et al., "Fumaric acid esters exert neuroprotective effects in neuroinflammation pathway via activation of the Nrf2 antioxidant pathway," *Brain* 134:678-692, Oxford University Press, England (2011).

Macari, E.R., et al., "Induction of human fetal hemoglobin via the NRF2 antioxidant response signaling pathway," *Blood* 117(22):5987-5997, American Society of Hematology, United States (2011).

McMahon, M., et al., "The Cap 'n' Collar Basic Leucine Zipper Transciption Factor Nrf2 (NF-E2 p45-related Factor 2) Controls Both Constitutive and Inducible Expression of Intestinal Detoxification and Glutathione Biosynthetic Enzymes," *Cancer Research* 61:3299-3307, American Association for Cancer Research, United States (2001).

Nguyen, T., et al., "Regulatory Mechanisms Controlling Gene Expression Mediated by the Antioxidant Reponse Element," *Annu. Rev. Pharmacol. Toxicol.* 43:233-260, Annual Reviews, United States (2003).

Oh, C.J., et al., "Dirnethylfumarate Attenuates Renal Fibrosis via NF-E2-Related Factor 2-Mediated Inhibition of Transforming Growth Factor-β/Smad Signaling," *PLoS One* 7(10):e45870, Public Library of Science, United States (2012).

Ramaswamy, S., et al, "Animal Models of Huntington's Disease," *ILAR Journal* 48(4):356-373, Oxford University Press, England (2007).

Riemekasten, G., et al., "Strong Acceleration of Murine Lupus by Injection of the SmD1[83-119] Peptide," *Arthritis & Rheumatism* 44(10):2435-2445, Wiley-Liss, Inc., United States (2001).

Sargent, J.L., et al., "A TGFβ-Responsive Gene Signature Is Associated with a Subset of Diffuse Scerloderma with Increased Disease Severity," *The Journal of Investigative Dermatology* 130:694-705, The Society for Investigative Dermatology, United States (2010).

(56) References Cited

OTHER PUBLICATIONS

Scannevin, R.H., et al., "Fumarates Promote Cytoprotection of Central Nervous System Cells against Oxidative Stress via Nuclear Factor (Erythroid-Derived 2)-Like 2 Pathway," *The Journal of Pharmacology and Experimental Therapeutics* 341(1):274-84, The American Society for Pharmacology and Experimental Therapeutics, United States (2012).
Scannevin, R.H., et al., "Neuroprotective Effects of BG-12 on Malonate-Induced Striatal Lesion Volume in Sprague-Dawley Rat Brain," poster P02.121, 64th Annual Meeting of the American Academy of Neurology, Apr. 21-28, 2012, New Orleans, LA, United States.
Shimozono, R., et al., "Nrf2 Activators Attenuate the Progression of Nonalcoholic Steatohepatitis-Related Fibrosis in a Dietary Rat Model," *Mol. Pharmacology* 84: 62-70, American Society for Pharmacology and Experimental Therapeutics, United States (2013).
Sobel, R.A.., et al., "The Immunopathology of Experimental Allergic Encephalomyelitis: I. Quantitative Analysis of Inflammatory Cells In Situ," *The Journal of Immunology* 132(5):2393-2401, American Association of Immunologists, United States (1984).
Sonnylal, S., et al., "Postnatal Induction of Transforming Growth Factor β Signaling in Fibroblasts of Mice Recapitulates Clinical, Histologic, and Biochemical Features of Scleroderma," *Arthritis & Rheumatism* 56(1):334-344, American College of Rheumatology, United States (2007).
Traugott, U., "Detailed Analysis of Early Immunopathologic Events during Lesion Formation in Acute Experimental Autoimmune Encephalomyelitis," *Cellular Immunology* 119:114-129, Academic Press, Inc., England (1989).
Trujillo, J., et al., "Renoprotective effect of the antioxidant curcumin: Recent findings," *Redox Biology* 1:448-456, Elsevier B.V., Netherlands (2013).
Tung, R., "The Development of Deuterium-Containing Drugs" *Innovations in Pharmaceutical Technology*, Issue 32:24-28, Samedan Ltd., England (2010).
Tuohy, V.K., et al., "A Synthetic Peptide From Myelin Proteolipid Protein Induces Experimental Allergic Encephalomyelitis," *The Journal of Immunology* 141 (4): 1126-1130, The American Association of Immunologists, United States (1988).
Üner, A.H., et al., "Characteristics of Auto Anti-idiotypic Antibodies Reactive with Antibodies Expressing the Pathogenic Idiotype, $Id^{LN}F_1$, in the (NZB x SWR)$F_1$ Model for Lupus Nephritis and its Parental Strains," *Journal of Autoimmunity* 11:233-40, Academic Press, England (1998).
Usategui, A., et al.,"A profibrotic role for thymic stromal lymphopoietin in systemic sclerosis," *Annals of the Rheumatic Diseases* 72:2018-2023, H.K. Lewis, England (Dec. 2013).
Van Dam, D. and De Deyn, P.P., "Animal models in the drug discovery pipeline for Alzheimer's disease," *British Journal of Pharmacology* 164:1285-1300, The British Pharmacological Society, Great Britain (2011).
Van Horssen, J., et al., "NAD(P)H:quinone oxidoreductase 1 expression in multiple sclerosis lesions," *Free Radic. Biol. Med.* 41:311-317, Elsevier Inc., United States (2006).
Van Muiswinkel, F.L., et al., "Expression of NAD(P)H:quinone oxidoreductase in the normal and Parkinsonian substantia nigra," *Neurobiology of Aging* 25:1253-1262, Elsevier Inc., United States (2004).
Van Muiswinkel, F.L. and Kuiperij, H.B., "The Nrf2-ARE Signaling Pathway: Promising Drug Target to Combat Oxidative Stress in Neurodegenerative Disorders," *Curr. Drug Targets-CNS & Neurol. Disord.* 4:267-281, Bentham Science Publishers Ltd., Netherlands (2005).
Vargas, M.R., et al., "Nrf2 Activation in Astrocytes Protects against Neurodegeneration in Mouse Models of Familial Amyotrophic Lateral Sclerosis," *The Journal of Neuroscience* 28(50):13574-13581, Society for Neuroscience, United States (2008).
Wang, X.J., et al., "Generation of a Stable Antioxidant Response Element-Driven Reporter Gene Cell Line and Its Use to Show Redox-Dependent Activation of Nfr2 by Cancer Chemotherapeutic Agents," *Cancer Research* 66(22):10983-10994, American Association for Cancer Research, United States (2006).

Wei, J., et al., "A synthetic PPAR-γ agonist triterpenoid ameliorates experimental fibrosis: PPAR-γ-independent suppression of fibrotic responses," *Annals of the Rheumatic Diseases* 73:446-454, H.K. Lewis, England (2014; published online Mar. 20, 2013).
Wu, M. and Varga, J., "In Perspective: Murine Models of Scleroderma," *Current Rheumatology Reports* 10:173-182, Current Science, United States (2008).
Yang, J-J, et al. "Nuclear erythroid 2-related factor 2: A novel potential therapeutic target for liver fibrosis," *Food and Chemical Toxicology* 59:421-427, Elsevier Ltd., England (2013).
Foster, A. B., "Deuterium isotope effects in the metabolism of drugs and xenobiotics: Implications for drug design," *Advances in Drug Research* 14: 1-40, Academic Press, England (1985).
Shiotsuki, M., et al., "Reaction of Ru(1-7-η-cyclooctatriene)($η^2$-dimethyl fumarate)$_2$ with Monodentate and Bidentate Phosphines: A Model Reaction of Catalytic Dimerization of Alkenes," *Organometallics* 19(26): 5733-5743, American Chemical Society, United States (2000).
Tajima, S., et al., "Fragmentation mechanism of dimethyl maleate and fumarate by electron impact," *International Journal of Mass Spectrometry and Ion Processes* 75: 147-157, Elsevier Science Publishers B.V., Netherlands (1987).
Zacharias, N.M., et al., "Real-Time Molecular Imaging of Tricarboxylic Acid Cycle Metabolism in Vivo by Hyperpolarized 1-$^{13}$C Diethyl Succinate," *Journal of the American Chemical Society* 134(2): 934-943, American Chemical Society, United States (2011).
International Search Report for International Application No. PCT/US2013/077248, European Patent Office, Netherlands, dated Mar. 21, 2014.
Co-pending U.S. Appl. No. 14/136,990, inventor Jianhua Chao, filed Dec. 20, 2013 (Not Published).
Belcher, J.D., et al., "Heme oxygenase-1 is a modulator of inflammation and vaso-occlusion in transgenic sickle mice," *The Journal of Clinical Investigation* 116(3):80816, American Society for Clinical Investigation, United States (2006).
Harbeson, S.L. and Tung, R.D., "Deuterium in Drug Discovery and Development," in *Annual Reports in Medicinal Chemistry*, vol. 46, Chapter 24, pp. 403-417, Concert Pharmaceuticals, Inc., Lexington, MA, USA (2011).
Gant, T.G., "Using Deuterium in Drug Discovery: Leaving the Label in the Drug," *Journal of Medicinal Chemistry*, American Chemical Society, United States, Dec. 2, 2013 (Epub ahead of print).
U.S. Appl. No. 14/264,653, inventor Ralf Gold, filed Apr. 29, 2014 (Not Published).
U.S. Appl. No. 14/119,373, inventors Dawson, K., et al., filed Feb. 18, 2014 (Not Published).
U.S. Appl. No. 14/124,562, inventors Guzowski, J., et al., §371 (c) date: Mar. 11, 2014 (Not Published).
U.S. Appl. No. 13/578,430, inventors Goelz, S., et al., filed Feb. 2, 2011 (Abandoned).
U.S. Appl. No. 14/209,480, filed Mar. 13, 2014 (Not Published).
U.S. Appl. No. 14/209,584, filed Mar. 13, 2014 (Not Published).
U.S. Appl. No. 14/209,651, filed Mar. 13, 2014 (Not Published).
U.S. Appl. No. 14/209,712, filed Mar. 13, 2014 (Not Published).
U.S. Appl. No. 14/209,756, filed Mar. 13, 2014 (Not Published).
U.S. Appl. No. 14/209,823, filed Mar. 13, 2014 (Not Published).
U.S. Appl. No. 14/212,503, filed Mar. 14, 2014 (Not Published).
U.S. Appl. No. 14/212,685, filed Mar. 14, 2014 (Not Published).
U.S. Appl. No. 14/213,321, filed Mar. 14, 2014 (Not Published).
U.S. Appl. No. 14/213,399, filed Mar. 14, 2014 (Not Published).
U.S. Appl. No. 14/213,673, filed Mar. 14, 2014 (Not Published).
U.S. Appl. No. 13/955,580, filed Jul. 31, 2013 (Abandoned).
U.S. Appl. No. 13/957,063 filed Aug. 1, 2013 (Abandoned).
U.S. Appl. No. 13/957,295, filed Aug. 1, 2013 (Abandoned).
Allowed Claims for U.S. Appl. No. 13/957,117, filed Aug. 1, 2013.
Allowed Claims for U.S. Appl. No. 13/957,220, filed Aug. 1, 2013.
Litjens et al., 2004, "Pharmacokinetics of oral fumarates in healthy subjects", Br J Clin Pharm, 58:4, 429-432.
Sobieraj and Coleman, 2012, "Dimethyl fumarate: A fumaric acid ester under investigation for the treatment of relapsing-remitting multiple sclerosis", Formulary, 47:386-391.

(56) References Cited

OTHER PUBLICATIONS

Werdenberg et al., 2003, "Presystemic Metabolism and Intestinal Absorption of Antipsoriatic Fumaric Acid Esters", Biopharmaceutics & Drug Disposition, 24:259-273.
Written Opinion of the International Searching Authority for International Application PCT/US2013/077248, dated Jun. 21, 2015.
International Preliminary Report on Patentability for International Patent Application PCT/US2013/077248, International Bureau of WIPO, Switzerland, dated Jun. 23, 2015.
Jiang et al., "Application of Deuteration in Drug Research," Qilu Pharmaceutical Affairs, vol. 29, No. 11, p. 682-684; 2010 (with English Translation).
Alvarez-Perez, et al., Journal of the American Chemical Society, 2008, vol. 130, pp. 1836-1838, Supporting information S1-S66.
Shaharuzzaman et al., Tetrahedron: Asymmetry, 1995, vol. 6, No. 12, pp. 2929-2932.
Hirst et al., Journal of the American Chemical Society, 1997, vol. 119, pp. 7434-7439.
Eberson et al., Journal of the Chemical Society, Perkin Transactions 2, 1999, pp. 1865-1868.
El-Batta et al., Journal of Organic Chemistry, 2007, vol. 72, pp. 5244-5259.
Battersby et al., Journal of the Chemical Society, 1981, No. 13, pp. 645-647.
Sato, Wako Organic Square, 2010, No. 33, pp. 2-4 (with English Translation).

\* cited by examiner

DEUTERIUM SUBSTITUTED FUMARATE DERIVATIVES

BACKGROUND

TECFIDERA™ was recently approved by the U.S. Food and Drug Administration for the treatment of subjects with relapsing forms of multiple sclerosis. TECFIDERA™ contains dimethyl fumarate (DMF), which has the following structure:

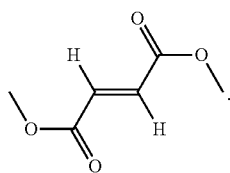

The first Phase 3 study, DEFINE (ClinicalTrials.gov identifier NCT00420212), demonstrated that DMF significantly reduced clinical relapses, accumulation of disability progression, and lesion number and volume compared with placebo after two years of treatment. See, e.g., Gold R, et al. *N Engl J Med* 2012; 367: 1098-107. These findings were supported by the results of the second phase 3 study, CONFIRM, which additionally evaluated subcutaneous glatiramer acetate as an active reference treatment (rater-blind). See, e.g., Fox R J, et al. *N Engl J Med* 2012; 367: 1087-97.

Preclinical and clinical data suggest dimethyl fumarate (DMF) has beneficial effects on neuroinflammation, neurodegeneration, and toxic-oxidative stress. See, e.g., Linker R. A., et al., *Brain* 2011; 134:678-92 and Scannevin R. H., et al., *J Pharmacol Exp Ther* 2012, 341:274-284. The beneficial effects of DMF and its primary metabolite, monomethyl fumarate (MMF), appear to be mediated, at least in part, through activation of the nuclear factor (erythroid-derived 2)-like 2 (Nrf2) antioxidant response pathway, an important cellular defense. Nrf2 is expressed ubiquitously in a range of tissues and, under normal basal conditions, is sequestered in the cytoplasm in a complex with Keap1 protein. However, when cells are under oxidative stress and overloaded with reactive oxygen or nitrogen species (ROS or RNS), or electrophilic entities, Nrf2 rapidly translocates to the nucleus, forms heterodimer with small protein Maf, then binds to the antioxidant response element resulting in increased transcription of several antioxidant and detoxifying genes including NQO-1, HO-1, and SRXN1. See, e.g., Nguyen et al., *Annu Rev Pharmacol Toxicol* 2003; 43:233-260; McMahon et al., *Cancer Res* 2001; 61:3299-3307. Sustained oxidative stress has been implicated in the pathogenesis of a variety of neurodegenerative diseases such as multiple sclerosis (MS), amyotrophic lateral sclerosis (ALS), Alzheimer's disease, and Parkinson's disease. For reviews, see, e.g., van Muiswinkel et al., *Curr. Drug Targets CNS—Neurol. Disord*, 2005; 4:267-281; Burton N. C. et al., *Comprehensive Toxicology*, 2010, 59-69.

DMF quickly gets absorbed in vivo and converted to MMF. The half-life of MMF was shown to be approximately 1 hour (0.9 h in rat at 100 mg/Kg oral dose). Both DMF and MMF are metabolized by esterases which are ubiquitous in the GI tract, blood and tissues.

DMF has demonstrated an acceptable safety profile in the DEFINE and CONFIRM studies. However, tolerability issues such as flushing and gastrointestinal events were observed. While these events are generally mild to moderate in severity, there remains a desire to reduce such events to further increase patient compliance and improve patient's quality of life. These mild adverse events could be the result of off-target events induced either by DMF or MMF and or the metabolites derived from them. For example, recent reports (Hanson et al., *J. Clin. Invest.* 2010, 120, 2910-2919; Hanson et al., *Pharmacol. Ther.* 2012, 136, 1-7.) indicate that MMF induced flushing is due to the activation of the G-protein-coupled receptor HCA2 (Hydroxy-carboxylic acid receptor 2, GPR109A).

There is a need for DMF analogs having an improved pharmacokinetic profile.

SUMMARY

Provided is a compound of formula (I):

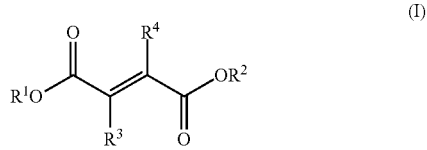

or a pharmaceutically acceptable salt thereof, wherein
each of $R^1$ and $R^2$, independently, is hydrogen, deuterium, deuterated methyl, deuterated ethyl, $C_{1-6}$ aliphatic, phenyl, 3-7 membered saturated or partially unsaturated monocyclic carbocyclic ring, 3-7 membered saturated or partially unsaturated monocyclic heterocyclic ring having 1-3 heteroatoms independently selected from nitrogen, oxygen, and sulfur, or a 5-6 membered heteroaryl ring having 1-3 heteroatoms independently selected from nitrogen, oxygen, and sulfur, and
each of $R^3$ and $R^4$, independently, is hydrogen or deuterium, provided that the compound of formula (I) contains at least one deuterium atom and that $R^1$ and $R^2$ are not hydrogen at the same time.

Also provided is a method of activating the Nrf2 pathway, comprising contacting cells with a sufficient amount of a compound of formula (I) described herein.

Also provided is a method of treating, prophylaxis, or amelioration of a disease (e.g., a neurodegenerative disease), comprising administering to a subject in need of treatment for the disease an effective amount of a compound of formula (I) described herein.

DETAILED DESCRIPTION

Definitions

Figure 1A:
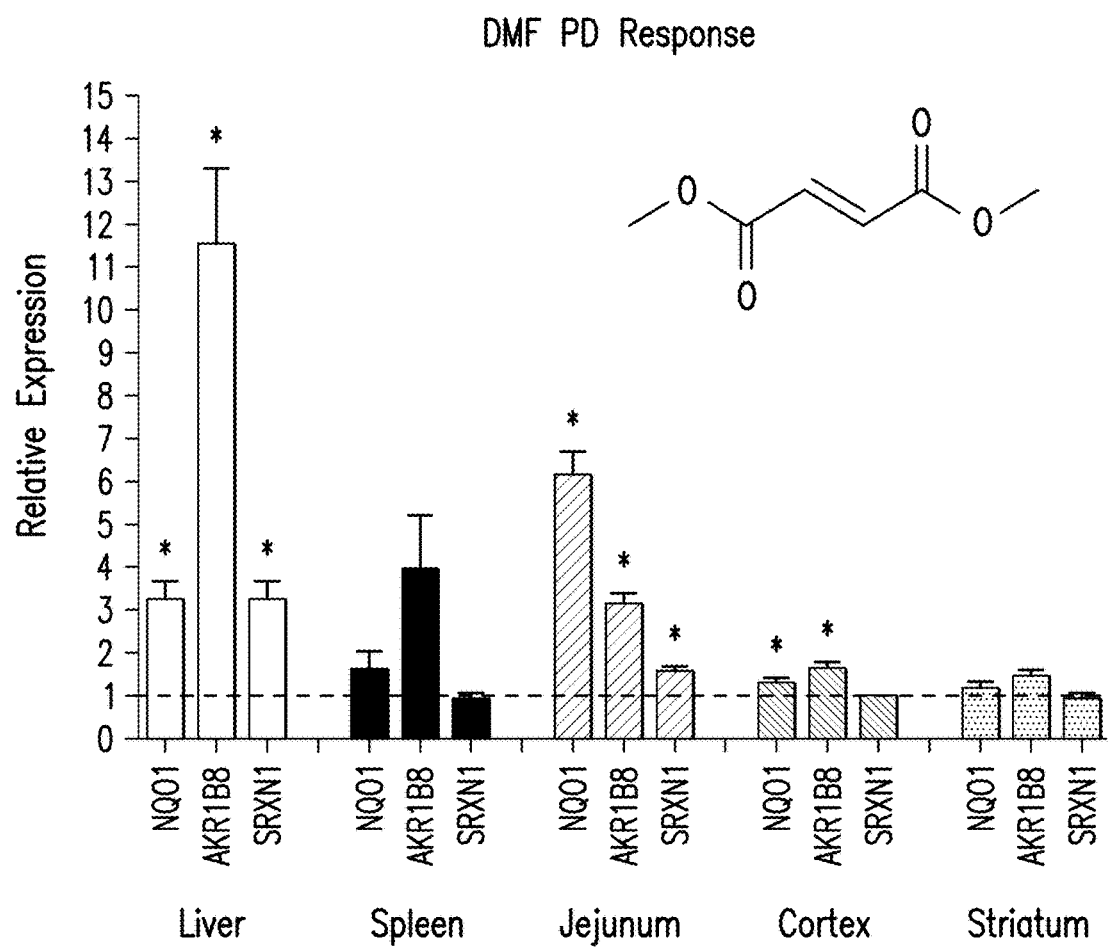
FIGS. 1(*a*)-(*c*) describe the pharmacodynamic (PD) response of DMF and compounds of Examples 1 and 2.

Certain terms are defined in this section; additional definitions are provided throughout the description.

The term "aliphatic" or "aliphatic group", as used herein, means a straight-chain (i.e., unbranched) or branched, substituted, or unsubstituted hydrocarbon chain that is completely saturated or that contains one or more units of unsaturation. Unless otherwise specified, aliphatic groups are optionally substituted and contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. Suitable aliphatic groups include, but are not limited to, linear or branched, substituted, or unsubstituted alkyl, alkenyl, alkynyl groups and hybrids thereof.

The term "carbocycle," "carbocyclic," or "cycloaliphatic," as used herein, means a monocyclic hydrocarbon that is completely saturated or that contains one or more units of unsaturation, but which is not aromatic (also referred to herein as "aryl"), that has a single point of attachment to the rest of the molecule. Unless otherwise specified, carbocyclic groups are optionally substituted. Examples include cycloalkyl and cycloalkenyl. In some embodiments, aliphatic groups contain 3-7 aliphatic carbon atoms. In some embodiments, aliphatic groups contain 4-6 aliphatic carbon atoms. In some embodiments, aliphatic groups contain 5-6 aliphatic carbon atoms, and in yet other embodiments, aliphatic groups contain 6 aliphatic carbon atoms.

The term "heteroaryl," as used herein, refers to groups having 5 to 6 ring atoms, sharing ρ electrons in a cyclic array; and having, in addition to carbon atoms, 1-3 heteroatoms. The term "heteroatom" refers to nitrogen, oxygen, or sulfur, and includes any oxidized form of nitrogen or sulfur, and any quaternized form of a basic nitrogen. Heteroaryl groups include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, and pyrazinyl. Unless otherwise specified, heteroaryl groups are optionally substituted.

As used herein, the terms "heterocycle," "heterocyclyl," "heterocyclic radical," and "heterocyclic ring" are used interchangeably and refer to a stable 5- to 7-membered monocyclic moiety that is either saturated or partially unsaturated, and having, in addition to carbon atoms, 1-3 heteroatoms, as defined above. When used in reference to a ring atom of a heterocycle, the term "nitrogen" includes a substituted nitrogen. As an example, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, but are not limited to, tetrahydrofuranyl, tetrahydrothiophenyl pyrrolidinyl, piperidinyl, pyrrolinyl, oxazolidinyl, piperazinyl, dioxanyl, dioxolanyl, diazepinyl, oxazepinyl, thiazepinyl, and morpholinyl.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Examples of optionally substituted groups that is, optional substituents include halogen, —NO$_2$, —CN, —OR, —SR, —N(R)$_2$, —C(O)R, —CO$_2$R, —N(R)C(O)OR, —C(O)N(R)$_2$, —OC(O)R, —N(R)C(O)R, —S(O)R, —S(O)$_2$R, or —S(O)$_2$N(R)$_2$. Each R is independently hydrogen or C$_{1-6}$ aliphatic; or two R groups attached to the same nitrogen are taken together with their intervening atoms to form an optionally substituted 3-7 membered saturated or partially unsaturated monocyclic heterocyclic ring having 1-2 heteroatoms, independently selected from nitrogen, oxygen, or sulfur. Optionally substituted groups of aliphatic can further include, but are not limited to, phenyl, 3-7 membered saturated or partially unsaturated monocyclic carbocyclic ring, 3-7 membered saturated or partially unsaturated monocyclic heterocyclic ring having 1-3 heteroatoms independently selected from nitrogen, oxygen, or sulfur, or a 5-6 membered heteroaryl ring having 1-3 heteroatoms independently selected from nitrogen, oxygen, or sulfur. For example, (cycloalkyl)alkyl, (cycloalkenyl)alkyl or (cycloalkyl)alkenyl, heterocyclylalkyl. Optionally substituted groups of phenyl, heterocycle, carbocycle, and heteroaryl can further include optionally substituted aliphatic groups.

The term "deuterium enrichment factor", as used herein, means the ratio between the isotopic abundance and the natural abundance of deuterium in a given sample of a compound.

In a compound of this invention, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3340 (50.1% deuterium incorporation) at each atom designated as deuterium in said compound. Deuterium incorporation percentage is defined as in a given sample of a compound the percentage of the molecules having deuterium at a particular position out of the total amount of the molecules including deuterated and non-deuterated.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The terms "deuterated methyl" and "deuterated ethyl," as used herein, means that the methyl group and the ethyl group contain at least one deuterium atom. Examples of deuterated methyl include —CDH$_2$, —CD$_2$H, and —CD$_3$. Examples of deuterated ethyl include, but are not limited to, —CHDCH$_3$, —CD$_2$CH$_3$, —CHDCDH$_2$, —CH$_2$CD$_3$.

As used herein, the term "pharmaceutically acceptable salt" refers to those salts which are, within the scope of sound medical judgment suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include, but not limited to, water, salt solutions (such as Ringer's solution), alcohols, oils, gelatins, and carbohydrates such as lactose, amylose or starch, fatty acid esters, hydroxymethylcellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The terms "activation" and "upregulation," when used in reference to the Nrf2 pathway, are used interchangeably herein.

The term "a drug for treating a neurological disease" refers to a compound that has a therapeutic benefit in a specified neurological disease as shown in at least one animal model of a neurological disease or in human clinical trials for the treatment of a neurological disease.

The term "treating" refers to administering a therapy in an amount, manner, or mode effective to improve a condition, symptom, or parameter associated with a disorder.

The term "prophylaxis" or the term "ameliorating" refers to preventing a disorder or preventing progression of a disorder, to either a statistically significant degree or to a degree detectable to one skilled in the art.

The terms "therapeutically effective dose" and "therapeutically effective amount" refer to that amount of a compound which results in prevention or delay of onset or amelioration of symptoms of a neurological disorder in a subject, or an attainment of a desired biological outcome, such as reduced neurodegeneration (e.g., demyelination, axonal loss, and neuronal death), reduced inflammation of the cells of the CNS, or reduced tissue injury caused by oxidative stress and/or inflammation in a variety of cells.

Compounds

Provided is a compound of formula (I)

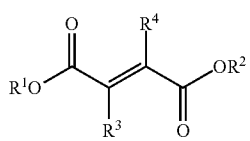

(I)

or a pharmaceutically acceptable salt thereof wherein
each of $R_1$ and $R_2$, independently, is hydrogen, deuterium, deuterated methyl, deuterated ethyl, $C_{1-6}$ aliphatic, phenyl, 3-7 membered saturated or partially unsaturated monocyclic carbocyclic ring, 3-7 membered saturated or partially unsaturated monocyclic heterocyclic ring having 1-3 heteroatoms independently selected from nitrogen, oxygen, and sulfur, or a 5-6 membered heteroaryl ring having 1-3 heteroatoms independently selected from nitrogen, oxygen, and sulfur, and each of $R^3$ and $R^4$, independently, is hydrogen or deuterium, provided that the compound of formula (I) contains at least one deuterium atom and that $R^1$ and $R^2$ are not hydrogen at the same time.

Also provided is a compound of formula (I)

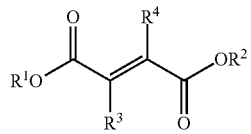

(I)

or a pharmaceutically acceptable salt thereof, wherein
each of $R^1$ and $R^2$, independently, is hydrogen, deuterium, deuterated methyl, deuterated ethyl, or $C_{1-6}$ aliphatic, and each of $R^3$ and $R^4$ independently, is hydrogen or deuterium, provided that the compound of formula (I) contains at least one deuterium atom and that $R^1$ and $R^2$ are not hydrogen at the same time.

In some embodiments, $R^1$ is hydrogen or —$CH_3$. In some embodiments, $R^1$ is —$CD_3$. In some embodiments, $R^1$ is —$CD_2CD_3$.

In some embodiments, $R^2$ is —$CH_2D$, —$CHD_2$, or —$CD_3$
In some embodiments, $R^2$ is H, —$CH_3$, —$CH_2D$, —$CHD_2$, or —$CD_3$.

In some embodiments, $R^1$ is hydrogen or —$CH_3$ and $R^2$ is —$CH_2D$, —$CHD_2$, or —$CD_3$.

In some embodiments, $R^1$ is —$CD_3$ and $R^2$ is —$CH_2D$, —$CHD_2$, or —$CD_3$.

In some embodiments, at least one of $R^3$ and $R^4$ is deuterium. In some embodiments, both of $R^3$ and $R^4$ are deuterium.

In some embodiments, at least one of $R^3$ and $R^4$ is deuterium and $R^2$ is hydrogen, —$CH_3$, —$CH_2D$, —$CHD_2$, or —$CD_3$. In some embodiments, both of $R^3$ and $R^4$ are deuterium and $R^2$ is hydrogen, —$CH_3$, —$CH_2D$, —$CHD_2$, or —$CD_3$.

In some embodiments, $R^1$ is —$CD_2CD_3$ and $R^2$ is H, —$CH_3$, —$CH_2D$, —$CHD_2$, or —$CD_3$ In some embodiments, the compound of formula (I) is ($^2H_6$)dimethyl fumaric acid ester, ($^2H_3$)methyl fumaric acid ester, ($^2H_3$)dimethyl fumaric acid ester, dimethyl fumaric(2, 3-$^2H_2$) acid ester, methyl fumaric(2,3-$^2H_2$) acid ester, ethyl fumaric(2,3-$^2H_2$) acid ester, ($^2H_3$)methyl fumaric(2,3-$^2H_2$) acid ester, ($^2H_6$)dimethyl fumaric(2,3-$^2H_2$) acid ester, methyl (2-morpholino-2-oxoethyl) fumaric(2,3-$^2H_2$) acid ester, methyl (4-morpholino-1-butyl) fumaric(2,3-$^2H_2$) acid ester, 2-(benzoyloxy)ethyl methyl fumaric(2,3-$^2H_2$) acid ester, 2-(benzoyloxy)ethyl ($^2H_3$)methyl fumaric acid ester, (S)-2-((2-amino-3-phenylpropanoyl)oxy)ethyl methyl fumaric(2,3-$^2H_2$) acid ester, or (S)-2-((2-amino-3-phenylpropanoyl)oxy)ethyl ($^2H_3$)methyl fumaric acid ester.

In some embodiments, the compound of formula (I) is more resistant to CYP450 enzymes as compared with compounds of similar structure but lacking deuterium substitution.

In some embodiments, the compound of formula (I) will have slightly altered and slower metabolism as compared with compounds of similar structure but lacking deuterium substitution.

In some embodiments, the compound of formula (I) will have longer duration of action, increased exposure, and/or improved side effect profile as compared with compounds of similar structure but lacking deuterium substitution.

($^2$H$_6$)Dimethyl fumaric acid ester (Example 1) and ($^2$H$_3$) methylfumaric acid ester (Example 2) have demonstrated longer half-life of 3 to 3.2 hours, respectively, compared to DMF and MMF in rat, when given an oral dose of 100 mg/kg.

($^2$H$_6$)Dimethyl fumaric acid ester (Example 1), dimethyl (2,3-$^2$H$_2$)fumaric acid ester (Example 4), and ($^2$H$_6$)dimethyl (2,3-$^2$H$_2$)fumaric acid ester (Example 8) have demonstrated higher oral exposure when compared to DMF at an equivalent oral dose of 50 mg/kg of DMF in the same study.

Methods of Making

Compounds of formula (I) can be synthesized, for example, using the following schemes.

Scheme A:

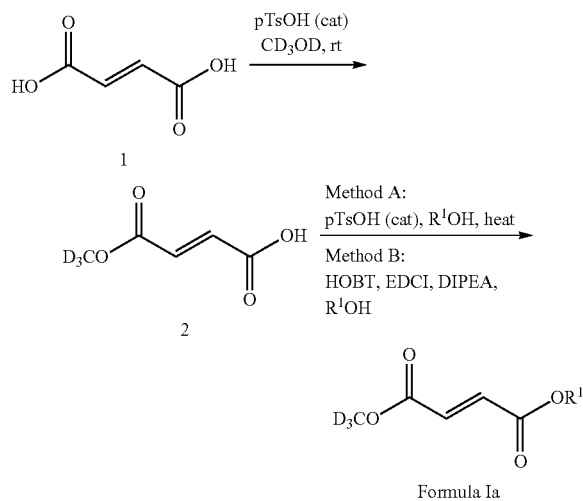

As depicted in Scheme A above, fumaric acid 1 can be converted to the monohydrogen ($^2$H$_3$)methyl fumaric acid ester 2 by reacting with deuterated methanol under the catalytic condition of p-toluenesulfonic acid at room temperature. At, for example, elevated temperature and similarly catalyzed by, e.g., p-toluenesulfonic acid, ester 2 can react with a variety of alcohols R$^1$OH (e.g., CH$_3$OH, CH$_2$DOH, CHD$_2$OH, CD$_3$OH, CD$_3$CH$_2$OH, or other deuterated alcohols) to provide deuterated fumaric acid esters of Formula Ia. Alternatively, treatment of compound 2 under coupling conditions, such as hydroxybenzotriazole (HOBT), 1-ethyl-3-(3-dimethylaminopropyl)carbodiimide (EDCI), and diisopropylethylamine (DIPEA) with alcohol R$^1$OH will afford acid esters of Formula Ia.

Compounds of formula (I) can contain deuterium connecting to one or both carbons of the double bond. See Scheme B below.

Scheme B:

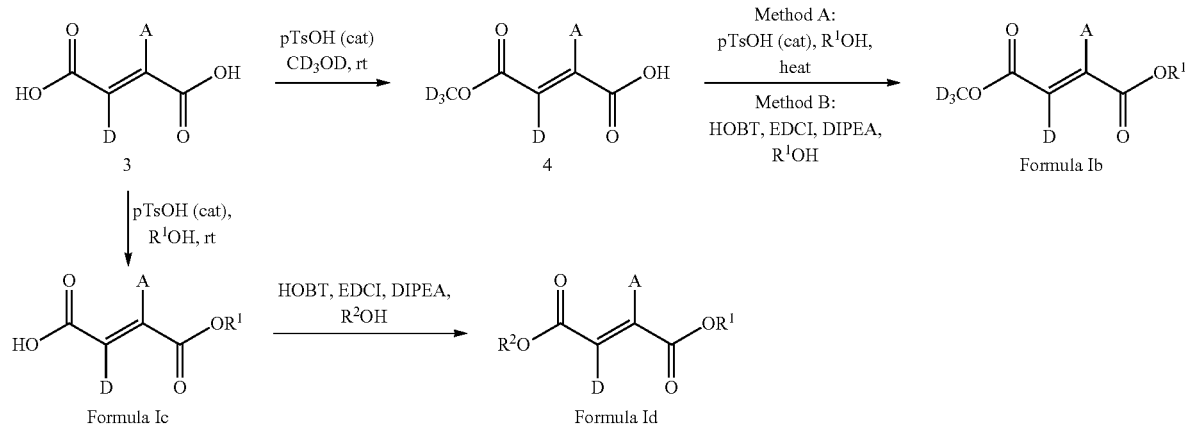

Starting with deuterated fumaric acid 3 (wherein A can be D or H; when A is D, the compound is available from Sigma-Aldrich (CAS#24461-32-3) and when A is H, the compound can be prepared according to *Tetrahedron Lett.* 1988, 29(36), 4577, compounds of Formula 1b can be prepared in two steps by first reacting with CD$_3$OD at room temperature under, e.g., the catalytic condition of p-toluene sulfonic acid followed by subsequent esterification with alcohol R$^1$OH (e.g., CH$_3$OH, CH$_2$DOH, CHD$_2$OH, CD$_3$OH, CD$_3$CH$_2$OH, or other deuterated alcohols) using either Method A or B. Compounds of Formula 1c can be prepared by reacting 3 with a variety of alcohol R$^1$OH under catalytic acid condition at ambient temperature. Treatment of compounds of Formula 1c under the conditions of HOBT, EDCI, and DiPEA will generate diester compounds of Formula 1d.

Pharmaceutical Compositions

The present invention provides pharmaceutical compositions comprising a compound of formula (I) or a compound of formula (I) in combination with a pharmaceutically acceptable excipient (e.g., carrier).

Compounds of formula (I) can be administered by any method that permits the delivery of the compound to a subject in need thereof. For instance, compounds of formula (I) can be administered orally, intranasally, transdermally, subcutaneously, intradermally, vaginally, intraaurally, intraocularly, intramuscularly, buccally, rectally, transmucosally, or via inhalation, or intravenously. For oral administration, compounds of formula (I) can be administered via pills, tablets, microtablets, pellets, micropellets, capsules (e.g., containing microtablets), suppositories, liquid formulations for oral administration, and in the form of dietary supplements. Oral formulations (e.g., tablets and microtablets) can be enteric coated. In some embodiments, the mean diameter of a microtablet is about 1-5 mm, e.g., about 1-3 mm or about 2 mm.

The compositions can include well-known pharmaceutically acceptable excipients, e.g., if the composition is an aqueous solution containing the active agent, it can be an isotonic saline, 5% glucose, or others. Solubilizing agents such as cyclodextrins, or other solubilizing agents well known to those familiar with the art, can be utilized as pharmaceutical excipients for delivery of the therapeutic compound. See, e.g., U.S. Pat. Nos. 6,509,376 and 6,436,992 for some formulations containing DMF and/or MMF.

Pharmaceutically acceptable carriers can be either solid or liquid. Solid form preparations include, but are not limited to, powders, tablets, pills, capsules, cachets, suppositories, and dispersible granules. A solid carrier can be one or more substance that may also act as diluents, flavoring agents, binders, preservatives, tablet disintegrating agents, or an encapsulating material.

Carriers or excipients generally serve as fillers, disintegrants, lubricants, and glidants. Examples of suitable carriers include, but are not limited to, magnesium carbonate, magnesium stearate, croscarmellose sodium, microcrystalline cellulose, talc, silica, sugar, lactose, pectin, dextrin, starch, gelatin, tragacanth, methylcellulose, sodium carboxymethylcellulose, a low melting wax, cocoa butter, and the like.

Some compounds may have limited solubility in water and therefore may require a surfactant or other appropriate co-solvent in the composition. Such co-solvents include, but are not limited to, Polysorbate 20, 60, and 80; Pluronic F-68, F-84, and P-103; cyclodextrin; and polyoxyl 35 castor oil. Such co-solvents can be employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, but are not limited to, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents can be employed at a level between about 0.01% and about 2% by weight.

Compounds of formula (I) can be administered in the form of a sustained or controlled release pharmaceutical formulation. Such formulation can be prepared by various technologies by a skilled person in the art. For example, the formulation can contain the therapeutic compound, a rate-controlling polymer (i.e., a material controlling the rate at which the therapeutic compound is released from the dosage form) and optionally other excipients. Some examples of rate-controlling polymers are hydroxy alkyl cellulose, hydroxypropyl alkyl cellulose (e.g., hydroxypropyl methyl cellulose, hydroxypropyl ethyl cellulose, hydroxypropyl isopropyl cellulose, hydroxypropyl butyl cellulose and hydroxypropyl hexyl cellulose), poly(ethylene)oxide, alkyl cellulose (e.g., ethyl cellulose and methyl cellulose), carboxymethyl cellulose, hydrophilic cellulose derivatives, and polyethylene glycol, and compositions as described in WO 2006/037342, WO 2007/042034, WO 2007/042035, WO 2007/006308, WO 2007/006307, and WO 2006/050730.

Nrf2 Pathway and Methods of Evaluating Nrf2 Activators

Nrf2 (Nuclear Factor-Erythroid 2-related factor 2; for sequence of the Nrf2, see Accession No. AAB32188) is the transcription factor that, upon activation by oxidative stress, forms heterodimer with small protein Maf, binds to the antioxidant response element (ARE), and activates transcription of Nrf2-regulated genes. The Nrf2/ARE pathway, a major determinant of phase II gene induction, has been well characterized for its role in hepatic detoxification and chemoprevention through the activation of phase II gene expression. ARE-regulated genes may also contribute to the maintenance of redox homeostasis by serving as endogenous anti-oxidant systems. At present, the list of Nrf2-regulated genes contains over 200 genes encoding proteins and enzymes involved in detoxification and antioxidant response (Kwak et al., J. Biol. Chem., 2003, 278:8135) such as, e.g., glutathione peroxidase, glutathione-S-transferases (GSTs), NAD(P)H:quinone oxidoreductases, now commonly known as nicotinamide quinone oxidoreductase 1 (NQO1; EC 1.6.99.2; also known as DT diaphorase and menadione reductase), NQO2, g-glutamylcysteine synthase (g-GCS), glucuronosyltransferase, ferritin, and heme oxygenase-1 (HO-1), as well as any one of the enzymes proteins listed in Table 1 in Chen & Kunsch, Curr. Pharm. Designs, 2004, 10:879-891; Lee et al., J, Biol. Chem., 2003, 278(14):12029-38, and Kwak, supra.

Accordingly, in some embodiments, the Nrf2-regulated gene which is used to assess the activation of the Nrf2 pathway is a phase II detoxification enzyme, an anti-oxidant enzyme, an enzyme of the NADPH generating system, and/or Nrf2 itself. Examples of the phase II detoxification enzymes include NQO1, NQO2, GST-Ya, GST-pi, GST-theta 2, GST-mu (1,2,3), microsomal GST 3, catalytic y-GCS, regulatory-GCS, microsomal epoxide hydrolase, UDP-glucuronosyltransferase, transaldolase, transketolase, and drug-metabolizing enzyme. Examples of the anti-oxidant enzymes include HO-1, ferritin (L), glutathione reductase, glutathione peroxidase, metallothionein I, thioredoxin, thioredoxin reductase, peroxiredoxin MSP23, Cu/Zn superoxide dismutase, and catalase. Examples of the enzymes of the NADPH generating system include malic enzyme, UDP-glucose dehydrogenase, malate oxidoreductase, and glucose-6-phosphate dehydrogenase.

Under basal conditions, Nrf2 is sequestered in the cytoplasm to the actin-bound Kelch-like ECH-associated protein 1 (Keap1; Accession No, NP_987096 for human Keap1), a Cullin3 ubiquitin ligase adaptor protein. More specifically, the N-terminal domain of Nrf2, known as Neh2 domain, is thought to interact with the C-terminal Kelch-like domain of Keap1. In response to xenobiotics or oxidative stress, Nrf2 is released from the Keap1/Nrf2 complex, thereby promoting nuclear translocation of Nrf2 and concomitant activation of ARE-mediated gene transcription. Keap1 function, in turn, requires association with Cullin3, a scaffold protein that positions Keap1 and its substrate in proximity to the E3 ligase Rbx1, allowing the substrate (Nrf2) to be polyubiquitinated and thus targeted for degradation. The exact mechanism of how the Keap1/Nrf2 complex senses oxidative stress remains poorly understood. Human Keap1 contains 25 cysteine residues that were hypothesized to function as sensors of oxidative stress; 9 of the cysteines are thought to be highly reactive (Dinkova-Kostova et al., PNAS, 2005, 102(12):4584-9). It was theorized but is not relied on for the purposes of this invention that alkylation of the Keap1 cysteines leads to a conformational change, resulting in the liberation of Nrf2 from Nrf2/Keap1/Cullin3 complexes, followed by nuclear translocation of the liberated Nrf2.

As mentioned above, pre-clinical studies have also shown that DMF is neuroprotective in animal models of neuroinflammation and neurodegeneration and that it defends against oxidative stress-induced injury. In addition to Linker R. A. et al. and Scannevin R. H. et al., supra, see also Ellrichmann G, et al. *PLoS One* 2011; 6:e36172, The neuroprotective effects of compounds of formula (I) can be evaluated in similar studies.

For example, the neuroprotective effects of compounds of formula (I) can be investigated in the malonate striatal lesion model of excitotoxicity. Malonate is a succinate dehydrogenase inhibitor, which is a mitochondrial enzyme that plays a central role in neuronal energy metabolism. Injection of malonate into the striatal region of the brain produces a lesion that is excitotoxic in character, as it can be blocked by systemic administration of N-methyl-D-aspartate (NMDA) receptor antagonists and has little inflammatory involvement. Intrastriatal malonate injection has been used as a model for acute neurodegeneration, and the potential therapeutic effects of test compounds of formula (I) can be explored in this setting. See, e.g., Scannevin R. H. et al., poster P02.121, 64$^{th}$ Annual Meeting of the American Academy of Neurology, Apr. 21-28, 2012, New Orleans, La., USA. The mouse cuprizone/rapamycin model of demyelination and neurodegeneration is another study that can be used to evaluate the neuroprotective effects of compounds of formula (I). Specifically, cuprizone is a neurotoxicant that when administered chronically to mice results in demyelination in the central nervous system, and has been used as a model to investigate modulation of remyelination. Administering rapamycin in addition to cuprizone results in more robust and consistent demyelination, presumably due to the anti-proliferative effect of stimulating the mammalian target of rapamycin (mTOR) receptor and pathway. The cuprizone plus rapamycin injury paradigm models prevalent pathologies (e.g., axonal transection, formation of ovoids and neuronal degeneration) associated with the human disease, and observation using this model provides unique insights into the mechanism of action of test compounds.

Diseases and Animal Models

ROS/RNS are most damaging in the brain and neuronal tissue, where they attack post-mitotic (i.e., non-dividing) cells such as glial cells and neurons, which are particularly sensitive to free radicals, leading to neuronal damage. Oxidative stress has been implicated in the pathogenesis of a variety of neurodegenerative diseases, including MS, ALS, Alzheimer's disease, Huntington disease, and Parkinson's disease. For review, see, e.g., van Muiswinkel et al., Curr. Drug Targets CNS—Neurol. Disord., 2005, 4:267-281. An anti-oxidative enzyme under control of Nrf2, NQO1 (NAD (P)H dehydrogenase, quinone 1), was reported to be substantially upregulated in the brain tissues of Alzheimer's disease and Parkinson's disease subjects (Muiswinkel et al., *Neurobiol. Aging*, 2004, 25:1253). Similarly, increased expression of NQO1 was reported in the ALS subjects' spinal cord (Muiswinkel et al., *Curr. Drug Targets—CNS. Neurol, Disord.*, 2005, 4:267-281) and in active and chronic lesions in the brains of patients suffering from MS (van Horssen et al., *Free Radical Biol. & Med.*, 2006, 41:313-311). These observations indicate that the Nrf2 pathway may be activated in neurodegenerative and neuroinflammatory diseases as an endogenous protective mechanism.

Activation of the Nrf2 pathway has demonstrated protective benefits in several neurodegenerative disease models. See, e.g., Calkins M J et al., *Toxicol Sci* 2010; 115:557-568.

In one aspect, the invention provides methods of treating, prophylaxis, or amelioration of a disease by administering (e.g., orally) to a subject in need thereof one or more compounds of formula (I). Examples of such diseases include neurodegenerative diseases including multiple sclerosis (MS) (e.g., relapsing-remitting MS, secondary progressive MS, primary progressive MS, progressive relapsing MS), amyotrophic lateral sclerosis (ALS), Alzheimer's disease, Parkinson's disease and Huntington's disease.

Other examples of neurodegenerative diseases include acute haemorrhagic leucoencephalomyelitis, Hurst's disease, encephalomyelitis (e.g., acute disseminated encephalomyelitis), optic neuritis, spinal cord lesions, acute necrotizing myelitis, transverse myelitis, chronic progressive myelopathy, progressive multifocal leukoencephalopathy (PML), radiation myelopathy, HTLV-1 associated myelopathy, monophasic isolated demyelination, central pontine myelinolysis, leucodystrophy (e.g., adrenoleucodystrophy, metachromatic leucodystrophy, Krabbe's disease, Canavan's disease, Alexander's disease, Pelizaeus-Merbacher disease, vanishing white matter disease, oculodentodigital syndrome), inflammatory demyelinising polyneuropathy (e.g., chronic inflammatory demyelinating polyneuritis (CIDP), and acute inflammatory demyelinating polyneuropathy (AIDP)).

Additional examples of diseases suitable for the methods of the invention include Guillain-Barre syndrome (GBS), polyneuritis, myasthenia gravis (MG), Eaton Lambert Syndrome (ELS), and encephalomyelitis. These disorders may be co-presented with, and possibly aggravated by diabetes, e.g., insulin-dependent diabetes mellitus (IDDM; type I diabetes), or other diseases.

Other examples of diseases suitable for the methods of the invention are diseases associated with fibrosis including Idiopathic Pulmonary Fibrosis (IPF), Scleroderma lung disease. Acute Lung Injury (ALI)/Acute respiratory Distress (ARDS), Chronic Asthma, Radiation-Induced Fibrosis Sarcoidosis, Pulmonary Hypertension, Bronchopulmonary Dysplasia (BPD), Lung Transplant Rejection, Pulmonary GVHD Complications, Interstitial pneumonia Syndrome (IPS) in transplant recipients, COPD, Silicosis, Asbestosis, Sarcoidosis (lung). Primary sclerosing cholangitis (PSC), Alcohol-induced hepatic fibrosis, Autoimmune hepatitis, Chronic viral hepatitis (HepB,C), Primary biliary cirrhosis (PBC), Non-alcohol Steatohepatitis (NASH), Liver transplant rejection, Hepatic complications of GVHD, Veno-occlusive disease in transplant recipients, Focal Segmental Glomerular Sclerosis (FSGS), Diabetic nephropathy, IgA nephropathy, Scleroderma, Renal complications of GVHD (AKI delayed graft function). Acute renal failure post CABG (AKI post CABG), Lupus nephritis, Hypertension-induced Renal Fibrosis, HIV-associated nephropathy, Peritoneal dialysis-induced peritoneal fibrosis, Retroperitoneal fibrosis, Idiopathic Glomerulosclerosis, Kidney transplant rejection, Alport syndrome. Restenosis, Subarachnoid hemorrhage (SAH), Heart transplant rejection, Stroke, Cosmetic surgery, Chronic wounds, Burns, Surgical adhesions, Keloids, Donor graft re-epithelialization, Myelofibrosis, Corneal transplant, LASIX, Trabeculectomy, Systemic sclerosis, Radiation induced fibrosis, Peripatellar Fibrosis, and Dupuytren's Contractures. In one aspect, the fibrosis disease is scleroderma.

Other diseases for which compounds of formula (I) may be therapeutically effective include inflammatory bowel disease, Crohn's disease, lupus (e.g., Neuropsychiatry lupus), systemic Lupus erythematodes (SLE), asthma, Leber's disease, Devic's disease (NMO), Friedrich's Ataxia, mitochondrial Central Nervous System diseases, scleroderma, uveitis, anti-phospholipid antibody syndrome, polyarthritis (e.g., rheumatoid arthritis), polyarticular juvenile idiopathic arthritis, sickle cell disease, ankylosing spondylitis, myositis, atherosclerosis, diabetic peripheral neuropathy, head injury, stroke, HIV-dementia, myocardial infarction, angina pectoris, cardiac insufficiency, psoriasis, psoriatic arthritis, Sjogren's syndrome, diabetes (e.g., type 1 diabetes, diabetes mellitus type II, juvenile-onset diabetes), blistering skin diseases, sarcoidosis, osteoarthritis, ulcerative colitis, vasculitis, lung fibrosis, idiopathic pulmonary fibrosis (IPF), liver fibrosis, kidney fibrosis, acute kidney injury, chronic kidney disease—diabetic nephrophathy, graft-versus-host reactions, Hashimoto's thyroiditis, Grave's disease, pernicious anaemia, hepatitis (e.g., chronic acid (=lupoid) hepatitis, acute hepatitis, toxic hepatitis, alcohol-induced hepatitis, viral hepatitis, jaundice, liver insufficiency, and cytomegaloviral hepatitis), neurodermatitis, retinopathia pigmentosa, forms of mitochondrial encephalomyopathy, osteochondritis syphilitica (Wegener's disease), cutis marmorata (livedo reticularis), Behcet disease, panarteriitis, osteoarthritis, gout, artenosclerosis, Reiter's disease, pulmonary granulomatosis, types of encephalitis, endotoxic shock (septic-toxic shock), sepsis, pneumonia, anorexia nervosa, Rennert T-lymphomatosis, mesangial nephritis, post-angioplastic restenosis, reperfusion syndrome, cytomegaloviral retinopathy, adenoviral diseases (e.g., adenoviral colds, adenoviral pharyngoconjunctival fever and adenoviral ophthalmia), AIDS, post-herpetic or post-zoster neuralgia, mononeuropathia multiplex, mucoviscidosis, Bechterew's disease, Barett oesophagus, Epstein-Barr virus (EVB) infection, cardiac remodeling, interstitial cystitis, human tumour radiosensitisation, multiresistance of malignant cells to chemotherapeutic agents (multidrug resistance in chemotherapy), granuloma annulare and cancers (e.g., mamma carcinoma, colon carcinoma, melanoma, primary liver cell carcinoma, adenocarcinoma, kaposi's sarcoma, prostate carcinoma, leukaemia (e.g., acute myeloid leukaemia, multiple myeloma (plasmocytoma), Burkitt lymphoma and Castleman tumour)), chronic obstructive pulmonary diseases, PDGF induced thymidine uptake of bronchial smooth muscle cells, bronchial smooth muscle cell proliferation, Adrenal Leukodystrophy (ALD), Alcoholism, Alper's disease, Ataxia telangiectasia, Batten disease (also known as Spielmeyer-Vogt-Sjögren-Batten disease), Bovine spongiform encephalopathy (BSE), Cerebral palsy, Cockayne syndrome, Corticobasal degeneration, Creutzfeldt-Jakob disease, Familial Fatal Insomnia, Frontotemporal lobar degeneration, Kennedy's disease, Lewy body dementia, Neuroborreliosis, Machado-Joseph disease (Spinocerebellar ataxia type 3), Multiple System Atrophy, Narcolepsy, Niemann Pick disease, Pick's disease, Primary lateral sclerosis, Prion diseases, Progressive Supranuclear Palsy, Refsum's disease, Sandhoff disease, Schilder's disease. Subacute combined degeneration of spinal cord secondary to Pernicious Anaemia, Spinocerebellar ataxia, Spinal muscular atrophy, Steele-Richardson-Olszewski disease, Tabes dorsalis, Toxic encephalopathy, MELAS (Mitochondrial Encephalomyopathy: Lactic Acidosis; Stroke), MERRF (Myoclonic Epilepsy; Ragged Red Fibers), PEO (Progressive External Opthalmoplegia), Leigh's Syndrome, MNGIE (Myopathy and external ophthalmoplegia; Neuropathy; Gastro-Intestinal; Encephalopathy), Kearns-Sayre Syndrome (KSS), NARP, Hereditary Spastic Paraparesis, Mitochondrial myopathy, optic neuritis, progressive multifocal leucoencephalopathy (PML), or other hereditary disorders (e.g., leukodystrophies, Charcot-Marie-Tooth disease), Pyoderma Gangrenosum, Erosive Pustular Dermatosis of the Scalp, Sweet's Syndrome, Bowel-associated Dermatosis-arthritis Syndrome, Pustular Psoriasis, Acute Generalized Exanthematous Pustulosis, Keratoderma Blenorrhagicum, Sneddon-Wilkinson Disease, Amicrobial Pustulosis of the Folds, Infantile Acropustulosis, Transient Neonatal Pustulosis, Neutrophilic Eccrine Hidradenitis, Rheumatoid Neutrophilic Dermatitis, Neutrophilic Urticaria, Still's Disease, Erythema Marginatum, Unclassified Periodic Fever Syndromes/Autoinflammatory Syndromes, Bullous Systemic Lupus Erythematosus, Neutrophilic Dermatosis of the Dorsal Hands (Pustular Vasculitis), anaphylaxis, allergic rhinitis, allergic asthma, lung cancer, severe asphyxic episodes of asthma, acute lung injury, Acute Respiratory Distress Syndrome, ischemia reperfusion injury, septicemia with multiorgan failure, inderteminate colitis, sickle cell crisis, or acute chest syndrome.

In one aspect, the invention provides methods of treating, prophylaxis, or amelioration of a neurological disease by administering (e.g., orally) to a subject in need thereof one or more compounds of formula (I). In one aspect, the neurological disease is MS (e.g., relapsing-remitting MS, secondary progressive MS, primary progressive MS, progressive relapsing MS), amyotrophic lateral sclerosis (ALS), Alzheimer's disease, Parkinson's disease or Huntington's disease. In one aspect, the neurological disease is MS (e.g., relapsing-remitting MS, secondary progressive MS, primary progressive MS, progressive relapsing MS), in one aspect, the neurological disease is relapsing-remitting MS.

MS is an autoimmune disease with the autoimmune activity directed against central nervous system (CNS) antigens. The disease is characterized by inflammation in parts of the CNS, leading to the loss of the myelin sheathing around neuronal axons (demyelination), axonal loss, and the eventual death of neurons, oligodenrocytes, and glial cells.

For MS, compounds of formula (I) can be assayed in well-known MS animal model, such as Experimental Autoimmune Encephalomyelitis (EAE) (Tuohy et al., *J. Immunol*, 1988, 141:1126-1130, Sobel et al. *J. Immunol.*, 1984, 132:2393-2401, and Traugott, *Cell Immunol*, 1989 119:114-129). Chronic relapsing EAE provides a well established experimental model for testing agents that would be useful for the treatment of MS. The mouse EAE is an induced autoimmune demyelinating disease with many similarities to human MS in its clinical manifestations. Other animal models that can be used include Thieler's murine encephalomyelitis virus (TMEV)-induced demyelinating disease, murine hepatitis virus (MHV), Semliki Forest Virus, and Sindbis virus as described in, e.g., Ercoli et al., *J. Immunol.*, 2006, 175:3293-3298.

ALS is a progressive neurodegenerative disease characterized by loss of both upper and lower motor neurons leading to body and facial muscle weakness. Life expectancy is approximately 3 years post diagnosis. The unmet need is extremely high as Rilutek (riluzole) is the only approved disease modifier and offers only a modest benefit (extends survival by about 3 months). A commonly used animal model is the mouse model with ALS-linked SOD1 G93A mutation. It has been shown recently that activation of the Nrf2 pathway via genetic overexpression or pharmacological induction conferred benefit in an hSOD1 G93A animal model. See Vargas M. R., et al., *J. Neurosci.*, 2008, 28(50):13574-13581.

Alzheimer's disease is the most common form of dementia. It is characterized by
the development of extracellular amyloid-beta (Ab) plaques and intracellular neurofibrillary tangles (NFT), accompanied by decreased synaptic density, which eventually leads to widespread neurodegeneration, loss of synapses and failure of neurotransmitter pathways, particularly those of the basal forebrain cholinergic system. Alzheimer's disease patients display prominent cognitive deficits such as memory loss, executive dysfunctioning, and behavior and psychological symptoms associated with dementia including paranoid and elusional behavior, hallucinations, anxieties and phobias. Alzheimer's disease animal models commonly used include spontaneous models in various species, including senescence-accelerated mice, chemical and lesion-induced rodent models, and genetically modified models developed in *Drosophila melanogasier, Caenorhabditis elegans, Danio rerio* and rodents. For review, see, e.g., Van Dam et al, *Br. J, Pharmacol.* 2011, 164(4): 1285-1300 and Götz et al, *Nat. Rev. Neurosci.* 2008, 9:532-544.

Parkinson's disease is characterized by the loss of ~50-70% of the dopaminergic neurons in the substantia nigra pars compacta (SNc), a profound loss of dopamine (DA) in the striatum, and the presence of intracytoplasmic inclusions called Lewy bodies (LB), which are composed mainly of α-synuclein and ubiquitin. Although mutations in the α-synuclein gene have thus far been associated only with rare familial cases of Parkinson's disease, α-synuclein is found in all LBs. The main features of Parkinson's disease are tremor, rigidity, bradykinesia, and postural instability; however, these motor manifestations can be accompanied by nonmotor symptoms such as olfactory deficits, sleep impairments, and neuropsychiatric disorders. Parkinson's disease animal models can typically be divided into toxin-based (those produced by 6-hydroxydopamine (6-OHDA), 1-methyl-1,2,3,6-tetrahydropiridine (MPTP) rotenone, and paraquat) or genetic models such as those utilizing the in vivo expression, of Parkinson's disease-related mutations (e.g., those related to alpha-synuclein, PINK1, Parkin and LRRK2). For review, see, e.g., Blesa et al., *J Biomed. Biotech.* 2012, Article ID 845638, pages 1-10.

Huntington's disease (HD) is a neurodegenerative disorder caused by a genetic mutation in the IT15 gene, leading to cognitive dysfunction and abnormal body movements called chorea. HD is characterized by progressive neurodegeneration of the striatum but also involves other regions, primarily the cerebral cortex. Like other neurodegenerative diseases, HD animal models are typically either toxin-induced models or genetic models. Toxin-induced models (e.g., those based on 3-nitropropionic acid and quinolinic acid) are used to study mitochondrial impairment and excitotoxicity-induced cell death, which are both mechanisms of degeneration seen in the HD brain. The discovery of the HD genetic mutation that led to HD in 1993 has led HD animal models that are genetic-based. These models include transgenic and knock-out mice, as well as a modes that uses a viral vector to encode the gene mutation in certain areas of the brain. For review, see, e.g., Ramaswamy et al., *ILAR J* 2007; 48(9):356-373.

The subject is mammalian, and can be a rodent or another laboratory animal, e.g., a non-human primate. In one aspect, the subject is human.

A compound may be optionally tested in at least one additional animal model (see, generally, Immunologic Defects in Laboratory Animals, eds. Gershwin et al., Plenum Press, 1981), for example, such as the following: the SWR X NZB (SNF1) mouse model (Uner et al., J. Autoimmune Disease, 1998, 11(3):233-240), the KRN transgenic mouse (K/BxN) model (Ji et al., Immunol. Rev., 1999, 69:139); NZB X NZW (B/W) mice, a model for SLE (Riemekasten et al, Arthritis Rheum., 2001,) 44(10):2435-2445); the NOD mouse model of diabetes (Baxter et al, Autoimmunity, 1991, 9(1):61-67), etc.).

Combination Therapy

The invention further includes treating, prophylaxis, or amelioration of a subject having a neurodegenerative disease by combination therapy. For example, the method includes administering (e.g., orally) to a subject having or at risk of developing a neurodegenerative disease with a compound of formula (I) and one or more other compounds of formula (I) or one or more other therapeutic agents.

In one embodiment, the one or more other therapeutic agents is a disease modifying agent. In one embodiment, the one or more other therapeutic agents alleviate the side effects of the compound of formula (I). For example, if a compound of formula (I) causes side effects such as flushing or GI disturbance (e.g., diarrhea), the one or more other therapeutic agent can be a therapeutic agent that can reduce the flushing (e.g., aspirin) or GI disturbance (e.g., loperamide).

In one embodiment, the combination therapy requires orally administering two compounds wherein at least one of the two compounds is a compound of formula (I). In one embodiment, the subject cars be treated with two compounds of formula (I). In one embodiment, the subject can be treated with a compound of formula (I) and DMF, MMF, or a DMF/MMF prodrug.

In one embodiment, the first compound and the second compound may be administered concurrently (as separate compositions or together in a single dosage form) or consecutively over overlapping or non-overlapping intervals. In the sequential administration, the first compound and the second compound can be administered in any order. In some embodiments, the length of an overlapping interval is more than 2, 4, 6, 12, 24, 48 weeks or longer.

In one embodiment, the compound of formula (I) and the one or more other therapeutic agents can be used to treat MS. The one or more other therapeutic agents can be, e.g., interferon beta-1a (Avonex®, Rebif®), glatiramer (Copaxone®), modafinil, azathioprine, predisolone, mycophenolate, mofetil, mitoxantrone, natalizumab (Tysabri®), sphinogosie-1 phosphate modulator e.g., fingolimod (Gilenya®), and other drugs useful for MS treatment such as teriflunornide (Aubagio®), piroxicam, and phenidone.

In one embodiment, the compound of formula (I) and the one or more other therapeutic agents can be used to treat ALS. The one or more other therapeutic agents is an agent or agents known or believe to be effective for ALS treatment, e.g., riluzole and dexpramipexole.

In one embodiment, the compound of formula (I) and the one or more other therapeutic agents can be used to treat AD. The one or more other therapeutic agents is an agent or agents known or believe to be effective for Alzheimer's disease treatment, e.g., rosiglitazone, roloxifene, vitamin E, donepezil, tacrine, rivastigmine, galantamine, and memantine.

In one embodiment, the compound of formula (I) and the one or more other therapeutic agents can be used to treat Parkinson's disease. The one or more other therapeutic agents is an agent or agents known or believe to be effective for Parkinson's disease treatment include, but are not limited to, dopamine precursors such levodopa, dopamine agonists such as bromocriptine, pergolide, pramipexole, and ropinirole, MAO-B inhibitors such as selegiline, anticholinergic drugs such as benztropine, trihexyphenidyl, tricyclic antidepressants such as amitriptyline, amoxapine, clomipramine, desipramine, doxepin, imipramine, maprotiline, nortriptyline, protriptyline, amantadine, and trimipramine, some antihistamines such as diphenhydramine; antiviral drugs such as amantadine.

Useful drugs for treating, prophylaxis, or amelioration of symptoms of Huntington's disease further include, but are not limited to, selective serotonin reuptake inhibitors (SSRI) such as fluoxetine, paroxetine, sertraline, escitalopram, citalopram, fluvosamine; norepinephrine and serotoiun reuptake inhibitors (NSRI) such as venlafaxine and duloxetine.

Dosages

Pharmaceutical compositions provided by the present invention include, but are not limited to, compositions wherein the active ingredient is contained in a therapeutically effective amount, i.e., in an amount effective to achieve its intended purpose (reduce or prevent neurodegeneration or neuroinflammation). The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Nrf2 activation); presence of other diseases or other health-related problems; kind of concurrent treatment; and complications from any disease or treatment regimen. Other therapeutic regimens or agents, as mentioned above, can be used in conjunction with the methods and compounds of the invention.

In one embodiment, at least one compound of formula (I) or pharmaceutically acceptable salt thereof is administered in an amount and for a period of time sufficient to reduce or prevent neurodegeneration and neuroinflammation in the subject. In one embodiment, at least one compound is administered in an amount and for a period of time sufficient to reduce astrogliosis, demyelination, axonal loss, and/or neuronal death in the subject. In one embodiment, the at least one compound or pharmaceutically acceptable salt thereof is administered in an amount and for a period of time sufficient to provide neuroprotection (e.g., restoring or increasing myelin content) to the subject.

Methods of the invention may include treating, prophylaxis, or amelioration of the subject having a neurodegenerative disease with a therapeutically effective amount of at least one compound of formula (I), which can range from about 1 mg/kg to about 50 mg/kg (e.g., from about 2.5 mg/kg to about 20 mg/kg or from about 2.5 mg/kg to about 15 mg/kg). Effective doses will also vary, as recognized by those skilled in the art, dependent on route of administration, excipient usage, and the possibility of co-usage with other therapeutic treatments including use of other therapeutic agents. In one embodiment, an effective dose of a compound of formula (I) to be administered to a subject, for example orally, can be from about 0.1 g to about 1 g per day, for example, from about 200 mg to about 800 mg per day (e.g., from about 240 mg to about 720 mg per day; or from about 480 mg to about 720 mg per day; or about 480 mg per day; or about 720 mg per day).

The daily dose can range, but is not limited to, a total amount of about 60 mg to about 800 mg, about 60 mg to about 720 mg, 60 mg to about 500 mg, about 60 mg to about 480 mg, about 60 mg to about 420 mg, about 60 mg to about 360 mg, about 60 mg to about 240 mg, about 60 mg to about 220 mg, about 60 mg to about 200 mg, about 60 mg to about 180 mg, about 60 mg to about 160 mg, about 60 mg to about 140 mg, about 60 mg to about 120 mg, about 60 mg to about 100 mg, about 60 mg to about 80 mg, about 80 mg to about 480 mg, about 100 mg to about 480 mg, about 120 mg to about 480 mg, about 140 mg to about 480 mg, about 160 mg to about 480 mg, about 180 mg to about 480 mg, about 200 mg to about 480 mg, about 220 mg to about 480 mg, about 240 mg to about 480 mg, about 300 mg to about 480 mg, about 360 mg to about 480 mg, about 400 mg to about 480 mg, about 450 mg to about 500 mg, about 480 mg to about 500 mg, about 80 to about 400 mg, about 100 to about 300 mg, about 120 to about 180 mg, or about 140 mg to about 160 mg.

The daily dose(s) of one or more compounds of formula (I) may be administered in a single administration or in separate administrations of 2, 3, 4, or 6 equal doses. In one embodiment, the effective daily dose is about 720 mg per day and is administered in 3 equal doses to a subject in need thereof (i.e., three times a day, TID). In one embodiment, the effective daily dose is about 480 mg per day and is administered in 2 equal doses to a subject in need thereof (i.e., two times a day, BID). In one embodiment, the effective daily dose is about 480 mg per day and is administered in one dose to a subject in need thereof.

In one embodiment, the dosage form administered one or more times daily can contain, but is not limited to, a total amount of about 60 mg, about 80 mg, about 100 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400 mg, about 420 mg, about 450 mg, about 480 mg, about 500 mg, about 620 mg, about 640 mg, about 660 mg, about 680 mg, about 700 mg, about 720 mg, about 740 mg, about 760 mg, about 780 mg, about 800 mg, about 820 mg, or about 840 mg of one or more compounds of formula (I).

In one embodiment, the dosage form containing one or more compounds of formula (I) is orally administered to a subject in need of treatment, prophylaxis, or amelioration of MS. In another embodiment, the dosage form containing one or more compounds of formula (I) is orally administered to a subject in need of treatment of relapsing-remitting MS.

In one embodiment, the therapeutically effective dose of a compound of formula (I) is administered to a subject in need thereof for a period of time sufficient to reduce neurodegeneration and/or neuroinflammation, e.g., by at least 30%, 50%, 100% or higher over a control over a period of at least 5, 10, 12, 20, 40, 52, 100, or 200 weeks.

In one embodiment, the pharmaceutical composition is administered at least one hour before or after food is consumed by the subject in need thereof. In case the subject experiences side effects (e.g., flushing or GI discomfort), the subject can consume food shortly (e.g., 30 mins to an hour) before administered the pharmaceutical composition.

In one embodiment, the subject administered a compound of formula (I) may take one or more non-steroidal anti-inflammatory drugs (e.g., aspirin) before (for example, 10 minutes to an hour, e.g., 30 minutes before) taking the pharmaceutical composition. In one embodiment, the subject administered the pharmaceutical composition takes the one or more non-steroidal anti-inflammatory drugs (e.g., aspirin) to control side effects (e.g., flushing). In another embodiment, the one or more non-steroidal anti-inflammatory drugs is selected from a group consisting of aspirin, ibuprofen, naproxen, ketoprofen, celecoxib, MK-0524, and combinations thereof. The one or more non-steroidal anti-inflammatory drugs can be administered in an amount of about 50 mg to about 500 mg before taking the dosage form described above. In one embodiment, a subject takes 325 mg aspirin before taking each dosage form described above.

In one embodiment the pharmaceutical preparation further comprises administering to the subject a first dose of the pharmaceutical preparation for a first dosing period; and administering to the subject a second dose of the pharmaceutical preparation for a second dosing period. In one embodiment, the first dose is lower than the second dose (e.g., the first dose is about half of the second dose). In one embodiment, the first dosing period is at least one week (e.g., 1-4 weeks). In one embodiment, the first dose of the pharmaceutical preparation comprises about 120 mg of a compound of formula (I) and the pharmaceutical preparation is administered to the subject BID or TID for the first dosing period. In one embodiment, the second dose of the pharmaceutical preparation comprises about 240 mg of a compound of formula (I) and the pharmaceutical preparation is administered to the subject BID or TID (e.g., BID) for the second dosing period. In one embodiment, if the subject, after being administered the dose at the second dosing period, experiences more than expected level of side effects (e.g., flushing or a gastrointestinal disturbance), the subject can use a lower dose (e.g., the dose at the first dosing period) for a period (e.g., 1-4 weeks or more) sufficient to allow the side effects to decrease before returning to the dose at the second dosing period.

In one embodiment, the first dose of the pharmaceutical preparation comprises about 120 mg of a compound of formula (I) and the pharmaceutical preparation is administered to the subject once daily for at least one week, and the second dose of the pharmaceutical preparation comprises about 240 mg of a compound of formula (I) and the pharmaceutical preparation is administered to the subject once daily for at least two weeks.

In one embodiment, the subject is administered a first dose for one week and a second dose for a second dosing period of at least 48 weeks. In another embodiment, the subject is administered a first dose for one week and a second dose for a second dosing period of at least two years. In another embodiment, the subject is administered a first dose for one week and a second dose until the subject does not require treatment, prophylaxis, or amelioration of the disease or disorder (e.g., neurodegenerative disorder).

In order that the invention described herein may be more fully understood, the following examples are set forth. It should be understood that these examples are for illustrative purposes only and are not to be construed as limiting this invention in any manner.

EXAMPLES

As depicted in the Examples below, in certain exemplary embodiments, compounds are prepared according to the following general procedures. It will be appreciated that, although the general methods depict the synthesis of certain compounds of formula (I), the following general methods, and other methods known to one of ordinary skill in the art, can be applied to all compounds and subclasses and species of each of these compounds, as described herein.

Example 1: ($^2H_6$)dimethyl Fumaric Acid Ester

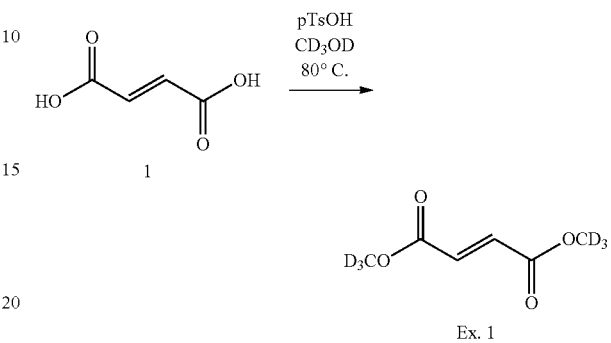

To a solution of fumaric acid 1 (1.16 g, 10 mmol) in $CD_3OD$ (1.8 g, 50 mmol, 5.0 eq) was added p-TsOH (0.17 g, 1.0 mmol, 0.1 eq). The reaction mixture was stirred at 80° C. for 6 hours, cooled to room temperature, diluted with EtOAc (50 mL), and washed with saturated $NaHCO_3$ (20 mL×2) and brine (20 mL). The organic layer was dried over anhydrous $Na_2SO_4$ and concentrated to give the titled compound, ($^2H_6$)dimethyl fumaric acid ester (0.97 g, yield: 65%) as a white solid. $^1H$ NMR (DMSO-$d_6$, 400 MHz) δ ppm: 6.78; (s, 2H); HPLC: 99.46%.

Example 2: ($^2H_3$)methyl Fumaric Acid Ester

To a solution of fumaric acid 1 (1.16 g, 10 mmol) in $CD_3OD$ (1.8 g, 50 mmol, 5.0 eq) was added p-TsOH (0.17 g, 1.0 mmol, 0.1 eq). The reaction mixture was stirred at rt for 48 hours, diluted with $H_2O$ (15 mL) and adjust pH to 10 with 1N aqueous $Na_2CO_3$. The mixture was extracted wife EtOAc (10 mL×3). The aqueous layer was adjusted to pH=1 with 1N HCl and extracted with EtOAc (20 mL×3). The combined organic layers were dried over anhydrous $Na_2SO_4$ and concentrated to give the crude product, which was recrystallized from THF (5 mL) to give the titled compound, ($^2H_3$)methyl fumaric acid ester (0.73 g, yield: 55%) as a white solid. $^1H$ NMR (CDCl$_3$, 400 MHz) δ ppm: 13.27; (br, 1H), 6.70; (s, 2H); ESI-MS (M+H)$^+$: 134.1; HPLC: 100.00%.

Example 3: (²H₃)dimethyl Fumaric Acid Ester

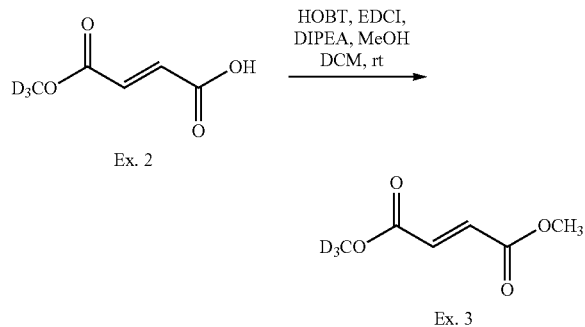

To a solution of (²H₃)methyl fumaric acid ester Ex.2, available from Example 2 (1 equiv.) in dichloromethane is added EDCI (1.5 equiv.), HOBt (1.5 equiv.), and DIPEA (2.0 equiv.). Methanol (1.2 equiv.) is added. The mixture is to be stirred overnight at room temperature, and then diluted with dichloromethane, to be washed with H₂O and brine. The organic layer should be dried over Na₂SO₄. Removal of solvent should afford the titled compound, which can be purified by recrystallization to give the pure product of (²H₃)dimethyl fumaric acid ester.

Example 4: Dimethyl fumaric(2,3-²H₂) Acid Ester

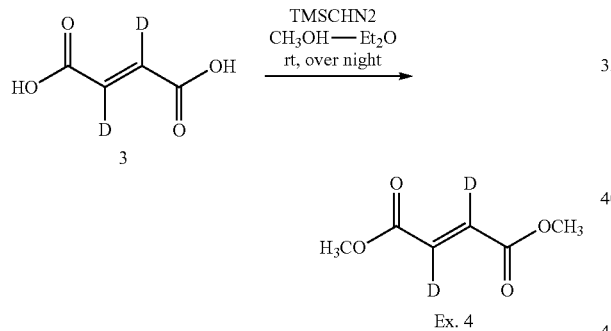

To a solution of fumaric(2,3-²H₂) acid 3 (0.2 g, 1.7 mmol) in methanol/diethyl ether (20/10 ml) was added (trimethylsilyl)diazomethane (3.2 mL, 6.4 mmol) dropwise. The mixture was stirred at room temperature overnight. Solvents were removed in vacuo, the residue was purified by column chromatography (PE/EA=80:1) to give the titled compound as a white solid (0.1 g, yield: 40%) ¹H NMR (300 MHz, CDCl3) δ 3.81; (s, 6H). LC-MS: m/z=147.1 [M+H]⁺. HPLC: 99.8%(214 ran); 100%(254 nm).

Example 5: Methyl fumaric(2,3-²H₂) Acid Ester

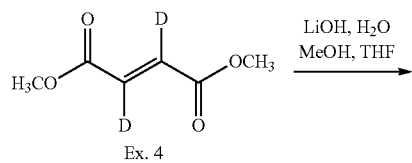

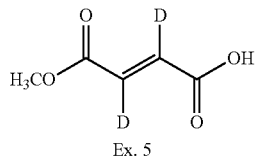

To a suspension of dimethyl fumaric(2,3-²H₂) acid ester Ex.4 (0.584 g, 4 mmol) and LiOH.H₂O (0.185 g, 4.4 mmol) in 40 mL of a mix-solvent system MeOH/THF/H₂O (2:1:1, v/v/v) was stirred at room temperature overnight. The reaction mixture was adjusted to pH=2 with a 2 N solution of hydrochloride acid, and extracted with EtOAc (40 mL×3). The combined organic extracts were dried over anhydrous Na₂SO₄. Removal of solvents under vacuo provided a crude product which was purified by prep-HPLC (Mobile phase A: water with 0.05% HCl, Mobile phase B: acetonitrile; Column: Synergi Max-RP 150×30 mm×4 um; Detection wavelength: 220 nm) to give the pure product of methyl fumaric (2,3-²H₂) acid ester (240 mg, 45%) as a white solid. ¹H NMR (400 MHz, DMSO-d6) δ: 3.74; (s, 3H). MS (ESI): m/z=131.0; [M+H]⁺, HPLC: 100% (220 nm).

Example 6: Ethyl fumaric(2,3-²H₂) Acid Ester

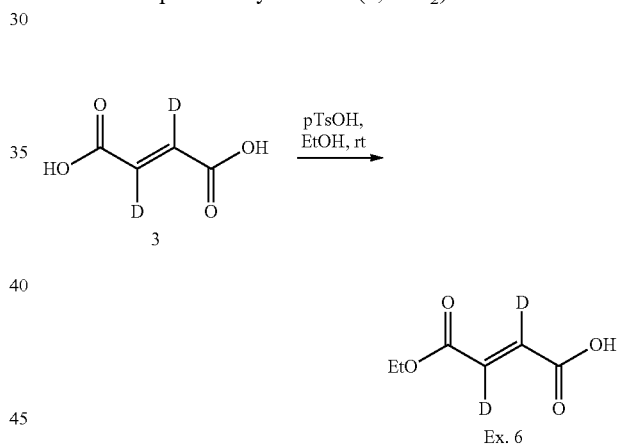

To a suspension of fumaric(2,3-²H₂) acid 3 (1.18 g, 10 mmol) in ethanol (2.3 g, 50 mmol) was added p-toluenesulfonic acid (0.17 g, 1 mmol). The reaction mixture was stirred at room temperature for 48 hours, diluted with water (20 mL) and adjusted to pH=10 using an aqueous Na₂CO₃ solution, and then the mixture was extracted with EtOAc (20 mL×3). The aqueous layer was adjusted to pH=1 using a 2N hydrochloride acid solution, and extracted with EtOAc (30 mL×3). The combined organic layers were dried over anhydrous Na₂SO₄ and concentrated in vacuo to give a crude product which was purified by prep HPLC (Mobile phase A: water with 0.05% HCl, Mobile phase B: acetonitrile; Column: Synergi Max-RP 150×30 mm×4 um; Detection wavelength: 220 nm) to give the titled compound (90 mg, 6.2%) as a white solid. ¹H NMR: (400 MHz, DMSO-d6) δ: 4.20; (q, J=7.0 Hz, 2H), 1.24; (t, J=7.0 Hz, 3H). MS (ESI): m/z=144.97[M+H]⁺, HPLC: Purity: 100%.

Example 7: (²H₂)methyl fumaric(2,3-²H₂) Acid Ester

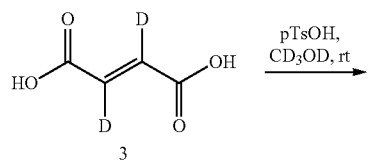

Ex. 7

To a suspension of fumaric(2,3-²H₂) acid 3 (0.826 g, 7 mmol) in CD₃OD (1.26 g, 35 mmol) was added p-toluenesulfonic acid (0.112 g, 0.7 mmol). The reaction mixture was stirred at room temperature for 48 hours, diluted with water (15 mL) and adjusted to pH=10 with a 1N aqueous Na₂CO₃ solution. The mixture was extracted with EtOAc (15 mL×3). The aqueous layer was acidified to pH=1 using a 1N hydrochloride acid solution and extracted with EtOAc (2.0 mL×3). The combined organic layers were dried over anhydrous Na₂SO₄ and concentrated to give a crude product. This crude product was combined with another batch and purified by prep-HPLC (Mobile phase A: water with 0.1% formic acid, Mobile phase B: acetonitrile; Column: YMC-Actus. Triart C18 150×30×5 um; Detection wavelength: 220 nm) to give titled compound (240 mg, 10% average yield) as a white solid. ¹H NMR: (400 MHz, DMSO-d6) δ: No proton signals. 13C NMR: (400 MHz, DMSO-d6) δ:166.12; (s, 1C), 165.49; (s, 1C), 134.98-134.48; (t 1C), 132.62-132.32; (t, 1C), 52.11-51.66; (m, 1C). MS (ESI): m/z=136.06[M+H]⁺. HPLC: Purity: 98.3%.

Example 8: (²H₆)dimethyl fumaric(2,3-²H₂) Acid Ester

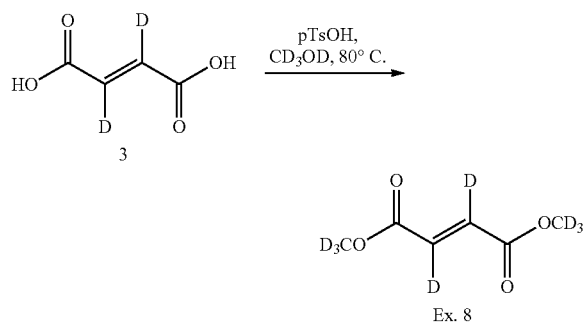

Ex. 8

To a suspension of fumaric(2,3-²H₂) acid 3 (2.95 g, 25 mmol) in CD₃OD (4.5 g, 125 mmol) was added p-toluenesulfonic acid (0.43 g, 2.5 mmol). The reaction mixture was stirred at 80° C. for 6 hour, cooled to room temperature, diluted with EtOAc (125 mL) and washed with a saturated NaHCO₃ (50 mL×2) and brine (50 mL). The organic layer was dried over anhydrous Na₂SO₄ and concentrated to give the titled compound (3.0 g, 79%) as a white solid. ¹H NMR: (400 MHz, CHLOROFORM-d) δ: No proton signals. ¹³C NMR: (400 MHz, CHLOROFORM-d) δ: 165.29 (s, 2C), 133.55-132.50; (m, 2C), 52.21-50.61; (m, 2C). MS (ESI): m/z=153.1; [M+H]⁺. HPLC: Purity: 99.88%.

Example 9: Methyl(2-morpholino-2-oxoethyl) fumaric(2,3-²H₂) Acid Ester

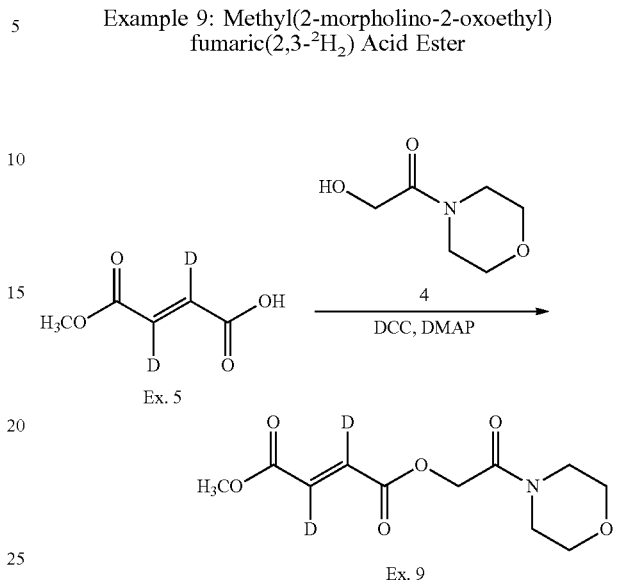

Ex. 9

A suspension of methyl fumaric(2,3-²H₂) acid ester Ex.5 (0.52 g, 4 mmol), 2-hydroxy-1-morpholinoethanone 4 (0.84 g, 6 mmol), DCC (N,N'-dicyclohexylcarbodiimide, 0.98 g, 4.8 mmol) and DMAP (4-dimethylaminopyridine, 0.098 g, 0.8 mmol) in CH₂Cl₂ was stirred at room temperature for 1 h. The precipitate was filtered off and the filtrate was concentrated in vacuo to give a crude product which was purified by prep-HPLC (Mobile phase A: water with 0.05% HCl, Mobile phase B: acetonitrile; Column: Synergi Max-RP 150×30 mm×4 um; Detection wavelength: 220 nm) to give the titled compound (52 mg, 10%) as a white solid. ¹H NMR: (400 MHz, CHLOROFORM-d) δ: 4.85; (s, 2H), 3.82; (s, 3H), 3.75-3.68; (m, 4H), 3.63; (br. s., 2H), 3.42; (br. s., 2H). HPLC: Purity: 97.94%. LCMS (ESI): m/z=259.7 [M+H]⁺.

Example 10: Methyl (4-morpholino-1-butyl) fumaric(2,3-²H₂) Acid Ester

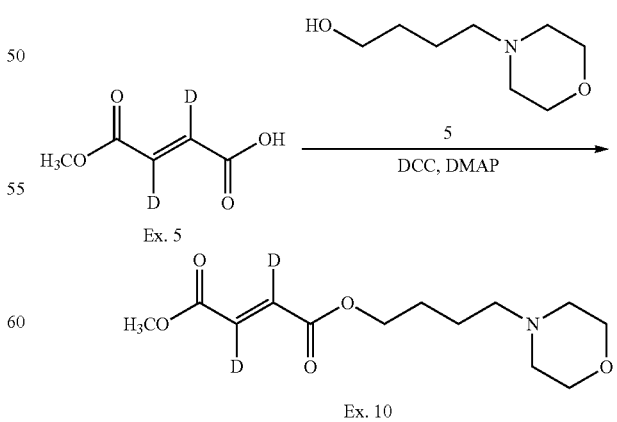

Ex. 10

To a mixture of methyl fumaric(2,3-²H₂) acid ester Ex.5 (0.06 g, 0.45 mmol), 4-morpholino-1-butanol 4 (0.094 g, 0.59 mmol) and DCC (0.140 g, 0.68 mmol) in anhydrous CH$_2$Cl$_2$ (2.5 mL) was added DMAP (0.011 g, 0.09 mmol) while cooling in an ice bath. The reaction mixture was stirred at room temperature for 2 h. The solids were filtered off and the filtrate was concentrated. The crude product was purified by preparative TLC to give the titled compound (100 mg, 90% purity). This product was combined with a different batch product (20 mg), recrystallized by PErEtOAc (10:1, v/v) to afforded the pure titled compound (66.5 mg, 28.6% avg) as a white solid. $^1$H NMR: (400 MHz, CHLOROFORM-d) δ: 4.24; (t, J=6.4 Hz, 2H), 3.82; (s, 3H), 3.73; (t, J=4.6 Hz, 4H), 2.45; (s, 4H), 2.38; (t, J=7.4 Hz, 2H), 1.80-1.69; (m, 2H), 1.65-1.54; (m, 2H). HPLC: Purity: 100%. MS: m/z=274.1 [M+H]$^+$.

Example 11: 2-(benzoyloxy)ethyl methyl fumaric(2,3-$^2$H$_2$) Acid Ester

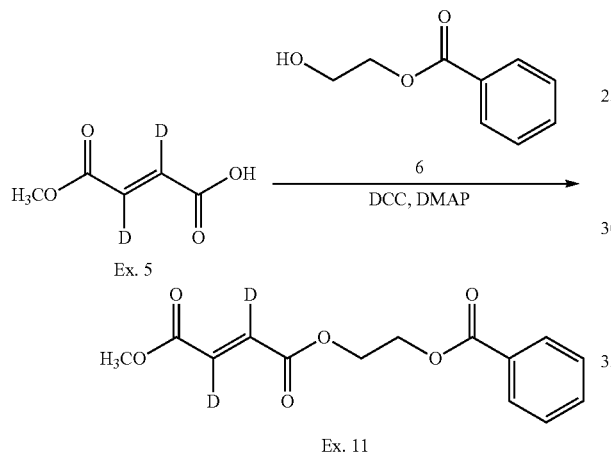

To a solution of methyl fumaric(2,3-$^2$H$_2$) acid ester Ex.5, available from Example 5 (1 equiv.) in dichloromethane is added 2-hydroxylethyl benzoate 6 (1.2 equiv.), DCC (1.5 equiv.) and DMAP (0.2 equiv.) at 0° C. The mixture is to be stirred at room temperature for a few hours, then the solids to be filtered off and the filtrate to be concentrated to a crude product. Purification of the crude either by preparative TLC or prep-HPLC should afford the pure titled product of 2-(benzoyloxy)ethyl methyl fumaric(2,3-$^2$H$_2$) acid ester.

Example 12: 2-(benzoyloxy)ethyl ($^2$H$_3$)methyl Fumaric Acid Ester

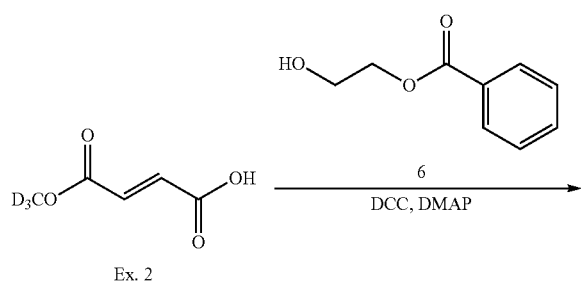

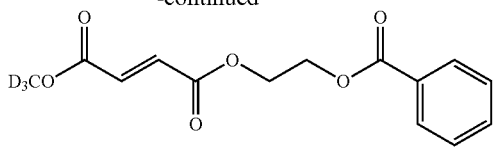

To a solution of ($^2$H$_3$)methyl fumaric acid ester Ex.2, available from Example 2 (1 equiv.) in dichloromethane is added 2-hydroxylethyl benzoate 6 (1.2 equiv.), DCC (1.5 equiv.) and DMAP (0.2 equiv.) at 0° C. The mixture is to be stirred at room temperature for a few hours, then the solids to be filtered off and the filtrate to be concentrated to a crude product. Purification of the crude either by preparative TLC or prep-HPLC should afford the pure titled product of 2-(benzoyloxy)ethyl ($^2$H$_3$)methyl fumaric acid ester.

Example 13: (S)-2-((2-amino-3-phenylpropanoyl)oxy)ethyl methyl fumaric (2,3-$^2$H$_2$) Acid Ester

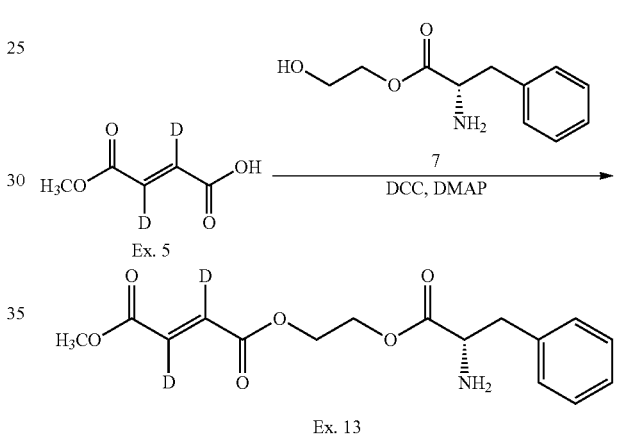

To a solution of methyl fumaric(2,3-$^2$H$_2$) acid ester Ex.5, available from Example 5 (1 equiv.) in dichloromethane is added (S)-2-hydroxylethyl 2-amino-3-phenylpropanoate 7 (1.2 equiv.), DCC (1.5 equiv.) and DMAP (0.2 equiv.) at 0° C. The mixture is to be stirred at room temperature for a few hours, then the solids to be filtered off and the filtrate to be concentrated to a crude product. Purification of the crude either by preparative TLC or prep-HPLC should afford the pure titled product of (S)-2-((2-amino-3-phenylpropanoyl)oxy)ethyl methyl fumaric(2,3-$^2$H$_2$) acid ester.

Example 14: (S)-2-((2-amino-3-phenylpropanoyl)oxy)ethyl ($^2$H$_3$)methyl Fumaric Acid Ester

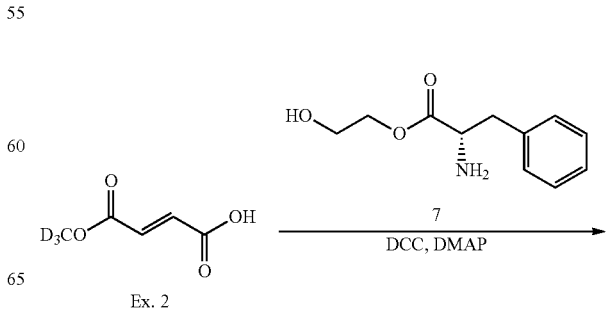

-continued

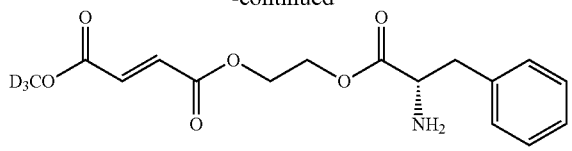

Ex. 14

To a solution of ($^2H_3$)methyl fumaric acid ester Ex.2, available from Example 2 (1 equiv.) in dichloromethane is added (S)-2-hydroxyethyl 2-amino-3-phenylpropanoate 7 (1.2 equiv.), DCC (1.5 equiv.) and DMAP (0.2 equiv.) at 0° C. The mixture is to be stirred at room temperature for a few hours, then the solids to be filtered off and the filtrate to be concentrated to a crude product. Purification of the crude either by preparative TLC or prep-HPLC should afford the pure titled product of (S)-2-((2-amino-3-phenylpropanoyl)oxy)ethyl ($^2H_3$)methyl fumaric acid ester.

Example 15: Evaluation of the Pharmacokinetic Properties of the Compound of Example 1 with DMF General procedure: Compounds were dosed in 0.5% HPMC suspension at 100 mg/Kg or a specific dose equivalent to male SD rats via oral gavage. Plasma samples were collected at 8 time points, 5 min, 15 min, 30 min, 1 h, 2 h, 4 h, 6 h and 12 h. Brain and CSF samples were collected at 30 min, 2 h, 4h, and 6 h. The samples were preserved by adding 2 mM PMSF and 1% acetic acid (final concentrations) during blood and CSF sample collection, and brain tissue homogenization. The concentration of the compounds was determined by LC/MS/MS.

Example 1 was dosed in 0.5% HPMC suspension @104 mg/kg (90 mg/kg MMF-eq) to male SD rats via oral gavage. Plasma samples were collected at 5 minutes, 15 minutes, 30 minutes, 1 hour, 2 hours, 4 hours, 6 hours and 12 hours and processed according to the above procedure. The concentration of D-MMF was determined by LC/MS/MS. Brain and CSF samples were collected at 30 min, 2 hr, 4 hr and 6 hr. The concentration of D-MMF was determined by LC/MS/MS.

Example 16: Evaluation of the Pharmacokinetic Properties of Example 1 with DMF DMF (50 mg/Kg) and Example 1 (52.2 mg/Kg, the equivalent of DMF dose) were suspended in corn oil, well stirred, dosed in a cassette format to three male SD rats via oral gavage. Plasma samples were collected at 0.08, 0.25, 0.5, 0.75, 1, 2, 4 and 7 hr. The blood samples were collected into pre-chilled vials containing 2 mM PMSF and 1% acetic acid (final concentrations). The concentration of the analytes, MMF (monomethyl fumaric acid ester) for DMF and ($^2H_3$)methyl fumaric acid ester Example 2 for Example 1, was determined by LC/MS/MS. The PK parameters were summarized in the table below:

| | analyte | dose [mg/kg] | route | $AUC_\infty$ [ng * h/ml] | $C_{max}$ [ng/ml] | $t_{max}$ [hr] | $t_{1/2}$ [hr] |
|---|---|---|---|---|---|---|---|
| Example 1 | Ex. 2 | 52.2 | PO | 7812 | 4667 | 0.25 | 1.7 |
| DMF | MMF | 50 | | 5413 | 3943 | 0.25 | 0.8 |

Figure 2:
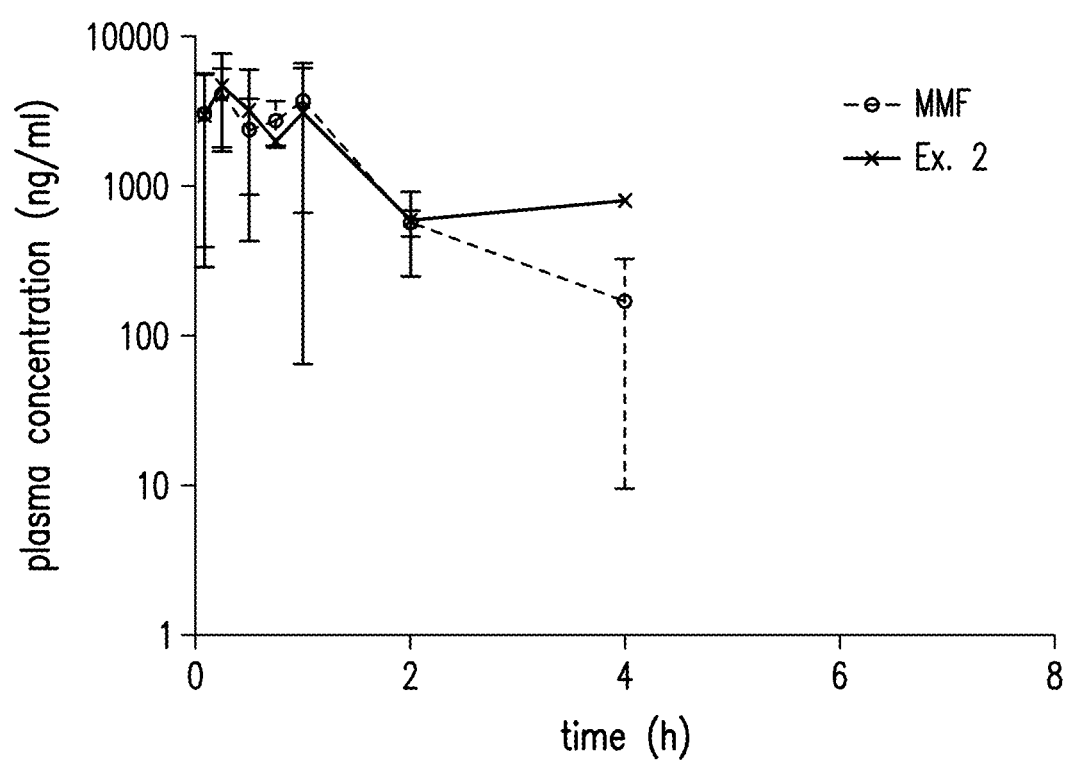
FIG. 2 describes pharmacokinetic properties of MMF and the compound of Example 2 after oral co-administration of DMF and the compound of Example 1.

FIG. 2 shows MMF and Example 2 PK after Oral Co-administration of DMF and Example 1.

Example 17: Evaluation of the Pharmacokinetic Properties of Example 4 with DMF DMF (50 mg/Kg) and Example 4 (50.7 mg/Kg, the equivalent of DMF dose) were suspended in corn oil, well stirred, dosed in a cassette format to three male SD rats via oral gavage. Plasma samples were collected at 0.08, 0.25, 0.5, 0.75, 1, 2, 4 and 7 hr. Blood samples were collected into pre-chilled vials containing 2 mM PMSF and 1% acetic acid (final concentrations). The concentration of the analytes, MMF (monomethyl fumaric acid ester) for DMF and methyl fumaric (2,3-$^2H_2$) acid ester Example 5 for Example 4 was determined by LC/MS/MS. The parameters were summarized in the table below:

| | analyte | dose [mg/kg] | route | $AUC_\infty$ [ng * h/ml] | $C_{max}$ [ng/ml] | $t_{max}$ [hr] | $t_{1/2}$ [hr] |
|---|---|---|---|---|---|---|---|
| Example 4 | Ex. 5 | 50.7 | PO | 14608 | 13630 | 0.75 | 0.43 |
| DMF | MMF | 50 | | 5866 | 5497 | 0.75 | 0.49 |

Figure 3:
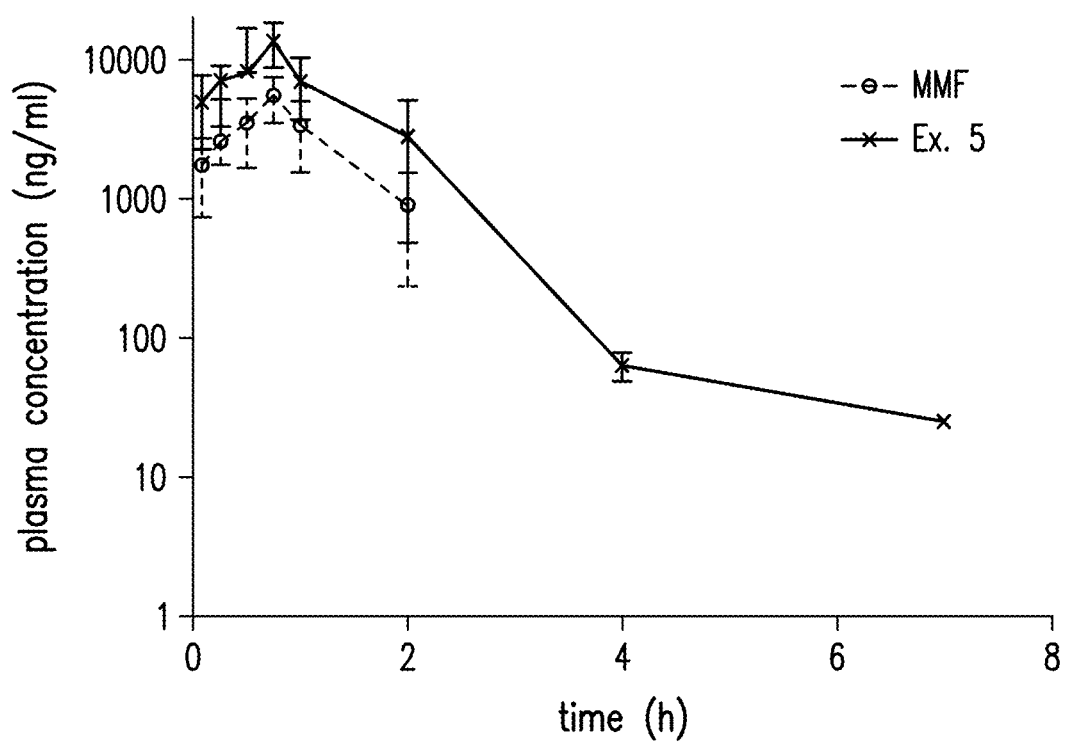
FIG. 3 describes pharmacokinetic properties of MMF and the compound of Example 5 after oral co-administration of DMF and the compound of Example 4.

FIG. 3 shows MMF and Example 5 PK after Oral Co-administration of DMF and Example 4.

Example 18: Evaluation of the Pharmacokinetic Properties of Example 8

DMF (50 mg/Kg) and Example 8 (53 mg/Kg, the equivalent of DMF dose) were suspended in corn oil, well stirred, dosed in a cassette format to three male SD rats via oral gavage. Plasma samples were collected at 0.08, 0.25, 0.5, 0.75, 1, 2, 4 and 7h. Blood samples were collected into pre-chilled vials containing 2 mM PMSF and 1% acetic acid (final concentrations). The concentration of analytes, MMF (monomethyl fumaric acid ester) for DMF and ($^2H_3$)methyl fumaric (2,3-$^2H_2$) acid ester Example 7 for Example 8, was determined by LC/MS/MS. The PK parameters were summarized in the table below:

| | analyte | dose [mg/kg] | route | $AUC_{0-7}$ [ng * h/ml] | $C_{max}$ [ng/ml] | $t_{max}$ [hr] | $t_{1/2}$ [hr] |
|---|---|---|---|---|---|---|---|
| Example 8 | Ex. 7 | 53 | PO | 12300 | 7850 | 0.22 | 5.92 |
| DMF | MMF | 50 | | 5977 | 5067 | 0.08 | 2.21 |

Figure 4:
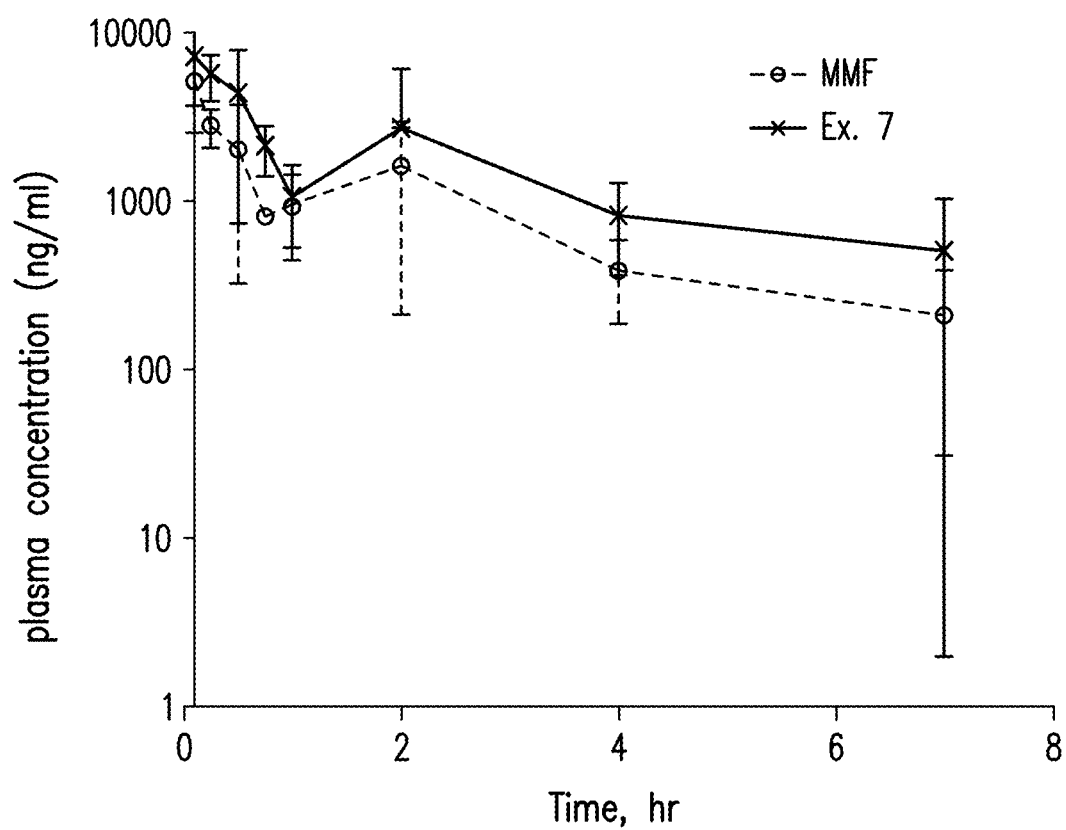
FIG. 4 describes pharmacokinetic properties of MMF and the compound of Example 7 after oral co-administration of DMF and the compound of Example 8.

FIG. 4 shows MMF and Example 7 PK after Oral Co-administration of DMF and Example 8.

Example 19: Evaluation of Nrf2 Activation Effects in a Luciferase Reporter Assay: Cell-Based Assay Human cancer cell line DLD-1 and breast cancer cell line MCF7 reporter stable cell lines were generated by transfection with a firefly luciferase reporter construct harboring the luciferase cDNA cloned downstream of eight catenated copies of the antioxidant response element (ARE) (GA-CAAAGCACCCGT; SEQ ID NO.:1). See Wang et al. Cancer Res. 2006; 66:10983-94.

To measure Nrf2 activation in the ARE-luciferase reporter cell lines, the cells were plated in 96-well plates at 20-50 k cells/well 24 hours prior to stimulation with the test compounds. The test compounds were prepared in dimethylsulfoxide (DMSO) and diluted with culture media to required concentrations (final DMSO concentrations <0.3%). The reporter cells were harvested 24 hours-48 hours after addition of the compounds and lysed for detection of luciferase activity. Luciferase activity in the lysates was monitored using the Bright-Glo Luciferase Assay System of Promega and Tecan Genios Pro plate reader.

Luciferase induction in the compound-treated cells was calculated as fold change over the baseline activity detected in control cultures treated with DMSO-containing media.

Nrf2 Activation in DLD-1 and MCF-7 ARE-Luc Reporter Cell Line EC50 [uM] at 48 hr stimulation (d6-DMF: Example 1; d3-MMF: Example 2)

Maximum Nrf2 Activation Fold Change Upon Compound Stimulation:

|  | 24 hr Stimulation | | | | 48 hr Stimulation | | | |
| --- | --- | --- | --- | --- | --- | --- | --- | --- |
|  | DLD-1/ ARE-E2 | | MCF-7/ ARE-D3 | | DLD-1/ ARE-E2 | | MCF-7/ ARE-D3 | |
|  | Fold Change | @ [uM] | Fold Change | @ [uM] | Fold Change | @ [uM] | Fold Change | @ [uM] |
| DMF | 3 | 31 | 25 | 63 | 9 | 31 | 68 | 94 |
| MMF | 5 | 1000 | 75 | 1000 | 12 | 1000 | 94 | 750 |
| Example 1 | 2 | 31 | 29 | 63 | 8 | 31 | 65 | 94 |
| Example 2 | 6 | 1000 | 55 | 1000 | 14 | 1000 | 81 | 1000 |

The data above indicates that compounds of Examples 1 and 2 are able to activate ARE-dependent signaling of the luciferase reporter construct. This suggests the compounds are able to activate the Nrf2 signaling cascade and induce expression of genes downstream of the ARE.

Example 20: Evaluation of Nrf2 Activation Effects in a Cell Based Nuclear Translocation Assay DiscoverRx Nrf2-Keap1 Pathway biosensor assay was used to profile DMF, Example 1, Example 4, and Example 8.

The PathHunter® Nuclear Translocation assay detects translocation of a target protein to, or from, the nucleus. In this system, Prolink™ (PK), a small enzyme fragment, is fused to the protein of interest and Enzyme Acceptor (EA) is localized in the nucleus. Activation of the signaling pathway induces the target protein to either transit into the nucleus, thus forcing complementation of the PK and EA fragments, or out of the nucleus, hindering complementation of the fragments.

Assay Protocol (Nrf2-Keap1):

PathHunter Pathway cell lines were expanded from freezer stocks according to standard procedures. 5000 cells were seeded in Cell Plating Reagent 0 (containing 1% FBS) to a total volume of 20 μL into white walled, 384-well microplates and incubated for the overnight prior to testing.

For Agonist determination, cells were incubated with sample to induce response. Dilution of sample stocks was performed to generate 100× sample in DMSO. Intermediate dilution of sample stocks was performed to generate 5× sample in assay buffer (Cell Plating Reagent 0 containing 1% FBS). 5 μL of 5× sample was added to cells and incubated at room temperature for 6 hours. Vehicle concentration was 1%.

Assay signal was generated through a single addition of 25 μL (100% v/v) of PathHunter Flash Detection reagent, followed by a one hour incubation at room temperature. Microplates were read following signal generation with a PerkinElmer Envision™ instrument for chemiluminescent signal detection.

Compound activity was analyzed using CBIS data analysis suite (ChemInnovation, CA). For agonist mode assays, percentage activity was calculated using the following formula: % Activity=100%×(mean RLU of test sample−mean RLU of vehicle control)/(mean MAX RLU control ligand−mean RLU of vehicle control).

Assay Results:

| Nrf2 activation | DMF | Example 1 | Example 4 | Example 8 |
| --- | --- | --- | --- | --- |
| $EC_{50}$ (uM) | 5.40 | 6.57 | 4.78 | 7.97 |
| n | 2 | 2 | 2 | 1 |

Example 21: In Vivo Evaluation of NrF2 Activation

Figure 1B:
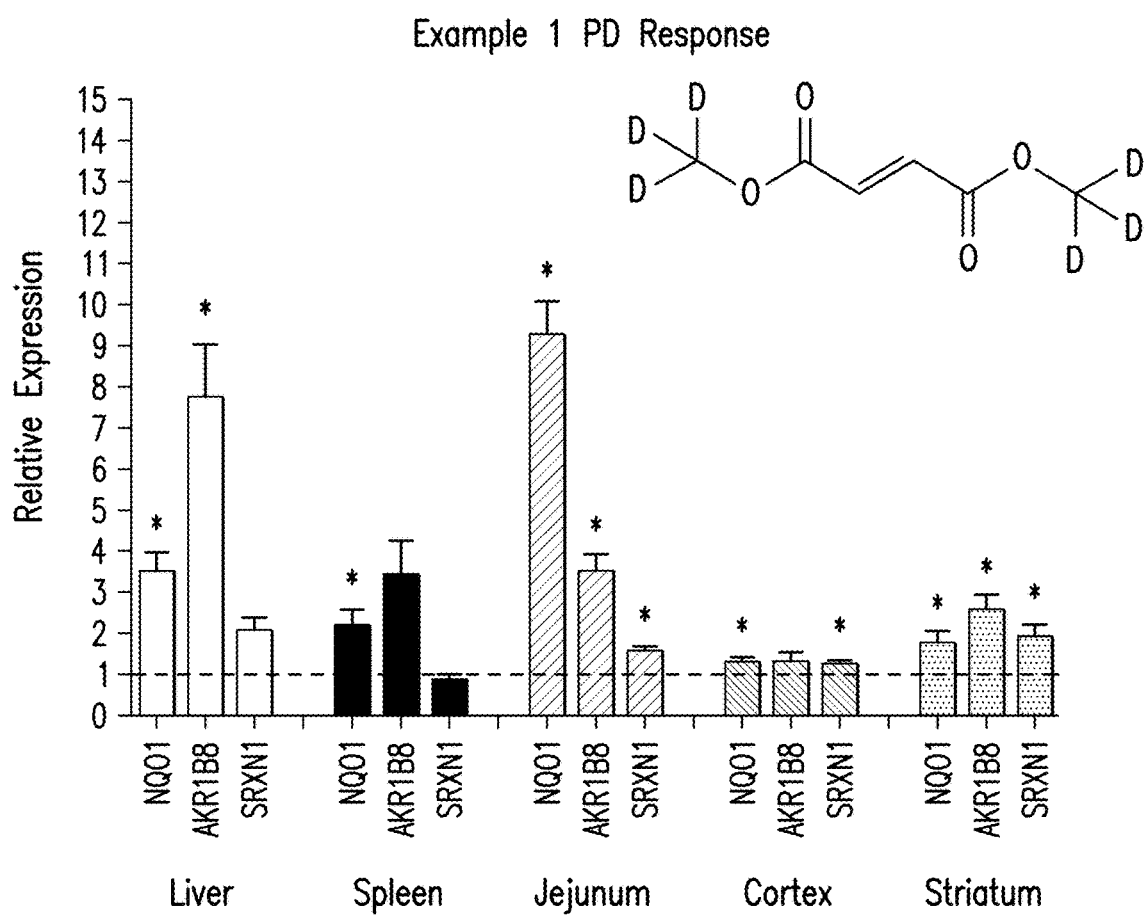
Figure 1C:
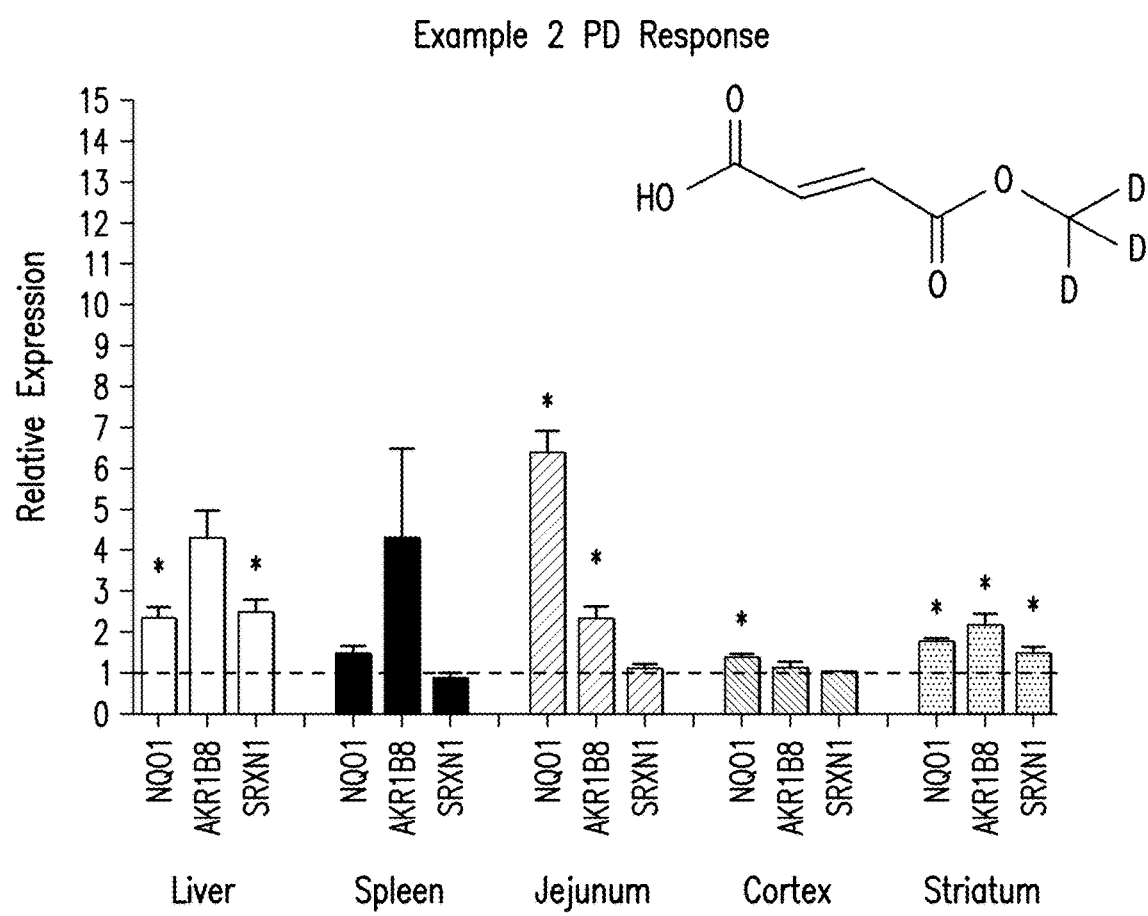

Test compounds were dosed either in suspension of 0.8% HPMC or corn oil via oral gavage to male SD rats (average weight of 250 mg, 6 animals per group, two groups), at a dose of 100 mg/kg equivalent of DMF (dosing volume: 5 ml/kg). After 30 minutes, the first group of animals was sacrificed via CO2 asphyxiation. 1.0 mL blood sample via cardiac bleed pipetted into chilled lithium heparin tubes with 10 mg sodium fluoride. Samples were centrifuged within 30 minutes at 4° C. for 15 minutes at 1500 G and plasma was transferred to chilled tubes and immediately frozen on dry ice, further kept at −70° C. until shipment for analysis. Brain was removed; sections were weighed and frozen until analysis. Brain and plasma samples were analyzed for ($^2H_3$) methylfumaric acid ester (MMP) exposure. After 6 hours, the second group of animals was sacrificed via CO2 asphyxiation. Brain, spleen, liver and jejunum were removed, flash frozen and placed on dry ice and maintained frozen until analysis. Sections of brain, spleen, liver, and jejunum were submitted for qPCR analysis of relative expression increase of Nrf2 responsive enzymes such as NQO-1, Akr1b8, and Sulfiredoxin-1. See results in FIGS. 1(a)-(c).

Having now fully described this invention, it will be understood by those of ordinary skill in the art that the same can be performed within a wide and equivalent range of conditions, formulation and other parameters without affecting the scope of the invention or any embodiment thereof.

All patents, patent applications and publications cited herein are fully incorporated by reference herein in their entirety. To the extent the material incorporated by reference contradicts or is inconsistent with the present specification, the present specification will supersede any such material.

The invention claimed is:

1. A compound of formula (I)

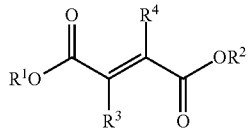

or a pharmaceutically acceptable salt thereof, wherein
(a) $R^1$ is hydrogen, deuterium, deuterated methyl, deuterated ethyl, $C_{1-6}$ aliphatic, phenyl, 3-7 membered saturated or partially unsaturated monocyclic carbocyclic ring, 3-7 membered saturated or partially unsaturated monocyclic heterocyclic ring having 1-3 heteroatoms independently selected from the group consisting of nitrogen, oxygen, and sulfur, or a 5-6 membered heteroaryl ring having 1-3 heteroatoms independently selected from the group consisting of nitrogen, oxygen, and sulfur,
(b) $R^2$ is —$CH_2D$, —$CHD_2$, or —$CD_3$,
(c) each of $R^3$ and $R^4$, independently, is hydrogen or deuterium, wherein at least one of $R^3$ and $R^4$ is deuterium, and
(d) the compound or pharmaceutically acceptable salt has an isotopic enrichment factor for each designated deuterium atom of at least 3500.

2. The compound or pharmaceutically acceptable salt of claim 1, wherein $R^1$ is hydrogen or —$CH_3$.

3. The compound or pharmaceutically acceptable salt of claim 1, wherein $R^1$ is —$CD_3$.

4. The compound or pharmaceutically acceptable salt of claim 1, wherein both of $R^3$ and $R^4$ are deuterium.

5. The compound or pharmaceutically acceptable salt of claim 1, wherein $R^1$ and $R^2$ are both —$CD_3$, and $R^3$ and $R^4$ are both deuterium.

6. A compound or pharmaceutically acceptable salt wherein the compound is ($^2H_6$)dimethyl fumaric(2,3-$^2H_2$) acid ester, methyl (2-morpholino-2-oxoethyl) fumaric(2,3-$^2H_2$) acid ester, methyl (4-morpholino-1-butyl) fumaric(2,3-$^2H_2$) acid ester, 2-(benzoyloxy)ethyl methyl fumaric(2,3-$^2H_2$) acid ester, 2-(benzoyloxy)ethyl ($^2H_3$)methyl fumaric acid ester, or (S)-2-((2-amino-3-phenylpropanoyl)oxy)ethyl methyl fumaric(2,3-$^2H_2$) acid ester, wherein the compound or pharmaceutically acceptable salt has an isotopic enrichment factor for each designated deuterium atom of at least 3500.

7. A pharmaceutical composition comprising
(a) a compound of formula (I)

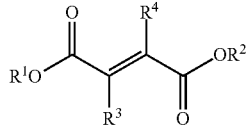

or a pharmaceutically acceptable salt thereof, wherein
each of $R^1$ and $R^2$, independently, is hydrogen, deuterium, deuterated methyl, deuterated ethyl, $C_{1-6}$ aliphatic, phenyl, 3-7 membered saturated or partially unsaturated monocyclic carbocyclic ring, 3-7 membered saturated or partially unsaturated monocyclic heterocyclic ring having 1-3 heteroatoms independently selected from the group consisting of nitrogen, oxygen, and sulfur, or a 5-6 membered heteroaryl ring having 1-3 heteroatoms independently selected from the group consisting of nitrogen, oxygen, and sulfur, and provided that $R^1$ and $R^2$ are not hydrogen at the same time,
each of $R^3$ and $R^4$ is deuterium, and
the compound or pharmaceutically acceptable salt has an isotopic enrichment factor for each designated deuterium atom of at least 3500; and
(b) a pharmaceutically acceptable carrier or excipient.

8. The pharmaceutical composition of claim 7, wherein $R^2$ is —$CH_2D$, —$CHD_2$, or —$CD_3$.

9. The pharmaceutical composition of claim 7, wherein $R^1$ and $R^2$ are both —$CD_3$.

10. The pharmaceutical composition of claim 7, wherein $R^1$ and $R^2$ are both —$CH_3$.

11. A method of treating, or amelioration of a neurodegenerative disease, comprising administering to a human subject in need of treatment for the neurodegenerative disease an effective amount of a compound of formula (I)

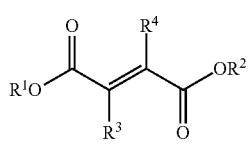

or a pharmaceutically acceptable salt thereof, wherein
(a) each of $R^1$ and $R^2$, independently, is hydrogen, deuterium, deuterated methyl, deuterated ethyl, $C_{1-6}$ aliphatic, phenyl, 3-7 membered saturated or partially unsaturated monocyclic carbocyclic ring, 3-7 membered saturated or partially unsaturated monocyclic heterocyclic ring having 1-3 heteroatoms independently selected from the group consisting of nitrogen, oxygen, and sulfur, or a 5-6 membered heteroaryl ring having 1-3 heteroatoms independently selected from the group consisting of nitrogen, oxygen, and sulfur, and provided that $R^1$ and $R^2$ are not hydrogen at the same time; and (b) each of $R^3$ and $R^4$, independently, is hydrogen or deuterium, wherein at least one of $R^3$ and $R^4$ is deuterium.

12. The method of claim 11, wherein the neurodegenerative disease is selected from the group consisting of Multiple Sclerosis, Amyotrophic Lateral Sclerosis, Parkinson's disease, Huntington's disease, Alzheimer's disease, acute haemorrhagic leucoencephalomyelitis, Hurst's disease, acute disseminated encephalomyelitis, optic neuritis, spinal cord lesions, acute necrotizing myelitis, transverse myelitis, chronic progressive myelopathy, progressive multifocal leukoencephalopathy (PML), radiation myelopathy, HTLV-1 associated myelopathy, monophasic isolated demyelination, central pontine myelinolysis, and leucodystrophy, chronic inflammatory demyelinating polyneuritis (CIDP), and acute inflammatory demyelinating polyneuropathy (AIDP).

13. The method of claim 12, which is a method of treating a neurodegenerative disease selected from the group consisting of Multiple Sclerosis, Amyotrophic Lateral Sclerosis, Parkinson's disease, Huntington's disease, and Alzheimer's disease.

14. The method of claim 13, which is a method of treating Multiple Sclerosis.

15. The method of claim 11, wherein the administering is orally.

16. The method of claim 15, wherein the effective amount is administered in a single administration.

17. The method of claim 15, wherein the effective amount is administered in separate administrations of 2, 3, 4, or 6 equal doses.

18. The method of claim 13, wherein the administering is orally.

19. The method of claim 18, wherein the effective amount is administered in a single administration.

20. The method of claim 18, wherein the effective amount is administered in separate administrations of 2, 3, 4, or 6 equal doses.

21. The method of claim 18, wherein the subject is administered a first dose for one dosing period and a second dose for a second dosing period.

22. The method of claim 11, wherein the compound or pharmaceutically acceptable salt has an isotopic enrichment factor for each designated deuterium atom of at least 3500.

23. The method of claim 11, wherein $R^2$ is —$CH_2D$, —$CHD_2$, or —$CD_3$.

24. The method of claim 11, wherein $R^1$ and $R^2$ are both —$CD_3$, and $R^3$ and $R^4$ are both deuterium.

25. The method of claim 11, wherein $R^1$ and $R^2$ are both —$CH_3$, and $R^3$ and $R^4$ are both deuterium.

26. The method of claim 13, wherein $R^1$ and $R^2$ are both —$CD_3$, and $R^3$ and $R^4$ are both deuterium.

27. The method of claim 13, wherein $R^1$ and $R^2$ are both —$CH_3$, and $R^3$ and $R^4$ are both deuterium.

28. The method of claim 14, wherein $R^1$ and $R^2$ are both —$CD_3$, and $R^3$ and $R^4$ are both deuterium.

29. The method of claim 14, wherein $R^1$ and $R^2$ are both —$CH_3$, and $R^3$ and $R^4$ are both deuterium.

* * * * *

```
                        SEQUENCE LISTING

<160> NUMBER OF SEQ ID NOS: 1

<210> SEQ ID NO 1
<211> LENGTH: 14
<212> TYPE: DNA
<213> ORGANISM: Artificial Sequence
<220> FEATURE:
<223> OTHER INFORMATION: antioxidant response element (ARE)

<400> SEQUENCE: 1
gacaaagcac ccgt                                                  14
```